(12) United States Patent
Taylor

(10) Patent No.: US 8,161,826 B1
(45) Date of Patent: Apr. 24, 2012

(54) ELASTICALLY STRETCHABLE FABRIC FORCE SENSOR ARRAYS AND METHODS OF MAKING

(75) Inventor: Geoffrey L. Taylor, Winnipeg (CA)

(73) Assignee: Stryker Corporation, Kalamazoo, MI (US)

( * ) Notice: Subject to any disclaimer, the term of this patent is extended or adjusted under 35 U.S.C. 154(b) by 486 days.

(21) Appl. No.: 12/380,845

(22) Filed: Mar. 5, 2009

(51) Int. Cl.
*G01L 1/22* (2006.01)
*G01L 3/00* (2006.01)
*G01D 7/00* (2006.01)

(52) U.S. Cl. ......... 73/862.044; 73/862.045; 73/862.042; 73/862.043; 73/862.041

(58) Field of Classification Search ............. 73/862.041–862.046
See application file for complete search history.

(56) References Cited

U.S. PATENT DOCUMENTS

| | | |
|---|---|---|
| 3,818,756 A | 6/1974 | Barron et al. |
| 3,996,922 A | 12/1976 | Basham |
| 4,033,332 A | 7/1977 | Hardway, Jr. et al. |
| 4,267,728 A | 5/1981 | Manley et al. |
| 4,308,872 A | 1/1982 | Watson et al. |
| 4,438,771 A | 3/1984 | Friesen et al. |
| 4,509,527 A | 4/1985 | Fraden |
| RE32,180 E | 6/1986 | Lewiner et al. |
| 4,633,237 A | 12/1986 | Tucknott et al. |
| 4,657,026 A | 4/1987 | Tagg |

(Continued)

FOREIGN PATENT DOCUMENTS

GB 2332063 6/1999

(Continued)

OTHER PUBLICATIONS

Laird Technologies. Nickel/Copper Polyester Taffeta. Product Specification for 3035-213. <Accessed Online> Sep. 6, 2011. <http://www.stockwell.com/data_sheets/esd_emi/3035213_nickel_polyester_taffeta.pdf>.*

(Continued)

*Primary Examiner* — Lisa Caputo
*Assistant Examiner* — Jonathan Dunlap
(74) *Attorney, Agent, or Firm* — Warner Norcross & Judd LLP

(57) ABSTRACT

Force or pressure transducer arrays have elastically stretchable electrically conductive polymer threads disposed in parallel rows and columns that contact at intersections thereof a piezoresistive material which has an electrical resistivity which varies inversely with pressure or force exerted thereon to form a matrix array of force or pressure sensor elements. The threads are fixed to a single one or pair of flexible elastically stretchable substrate sheets made of thin sheets of an insulating polymer such as PVC, or for greater elasticity and conformability to irregularly-shaped objects such as human body parts, an elastically stretchable fabric such as LYCRA or SPANDEX. Elastic stretchability of the sensor arrays is optionally enhanced by disposing either or both row and column conductive threads in sinuously curved, serpentine paths rather than straight lines.

38 Claims, 24 Drawing Sheets

U.S. PATENT DOCUMENTS

| | | |
|---|---|---|
| 4,738,266 A | 4/1988 | Thatcher |
| 4,827,763 A | 5/1989 | Bourland et al. |
| 4,986,277 A | 1/1991 | Sackner |
| 5,002,060 A | 3/1991 | Nedivi |
| 5,010,772 A | 4/1991 | Bourland et al. |
| 5,025,795 A | 6/1991 | Kunig |
| 5,060,174 A | 10/1991 | Gross |
| 5,062,169 A | 11/1991 | Kennedy et al. |
| 5,079,949 A * | 1/1992 | Tamori ............................ 73/172 |
| 5,128,880 A | 7/1992 | White |
| 5,178,151 A | 1/1993 | Sackner |
| 5,184,112 A | 2/1993 | Gusakov |
| 5,209,126 A | 5/1993 | Grahn |
| 5,253,656 A | 10/1993 | Rincoe et al. |
| 5,276,432 A | 1/1994 | Travis |
| 5,448,996 A | 9/1995 | Bellin et al. |
| 5,471,198 A | 11/1995 | Newham |
| 5,479,932 A | 1/1996 | Higgins et al. |
| 5,515,738 A * | 5/1996 | Tamori ...................... 73/862.46 |
| 5,571,142 A | 11/1996 | Brown et al. |
| 5,571,973 A * | 11/1996 | Taylot ...................... 73/862.046 |
| 5,590,650 A | 1/1997 | Genova |
| 5,600,108 A | 2/1997 | Newham |
| 5,623,760 A | 4/1997 | Newham |
| 5,633,627 A | 5/1997 | Newham |
| 5,640,145 A | 6/1997 | Newham |
| 5,654,694 A | 8/1997 | Newham |
| 5,684,460 A | 11/1997 | Scanlon |
| 5,722,287 A | 3/1998 | Forstein |
| 5,800,360 A | 9/1998 | Kisner et al. |
| 5,800,480 A * | 9/1998 | Augustine et al. ............. 607/96 |
| 5,865,755 A | 2/1999 | Golub |
| 5,964,720 A | 10/1999 | Pelz |
| 5,967,979 A | 10/1999 | Taylor |
| 5,993,400 A | 11/1999 | Rincoe et al. |
| 6,011,477 A | 1/2000 | Teodorescu et al. |
| 6,025,782 A | 2/2000 | Newham |
| 6,033,432 A * | 3/2000 | Augustine et al. ............. 607/96 |
| 6,047,203 A | 4/2000 | Sackner et al. |
| 6,147,592 A | 11/2000 | Ulrich et al. |
| 6,155,120 A | 12/2000 | Taylor |
| 6,180,893 B1 | 1/2001 | Salgo |
| 6,210,427 B1 * | 4/2001 | Augustine et al. ............. 607/96 |
| 6,216,545 B1 | 4/2001 | Taylor |
| 6,279,183 B1 | 8/2001 | Kummer et al. |
| 6,280,392 B1 | 8/2001 | Yoshimi et al. |
| 6,297,738 B1 | 10/2001 | Newham |
| 6,307,168 B1 | 10/2001 | Newham |
| D451,604 S | 12/2001 | Kasabach et al. |
| 6,341,504 B1 | 1/2002 | Istook |
| 6,377,177 B1 | 4/2002 | Broussard et al. |
| 6,396,004 B2 | 5/2002 | Salgo |
| 6,413,225 B1 | 7/2002 | Sackner et al. |
| 6,447,457 B1 | 9/2002 | Forstner et al. |
| 6,450,957 B1 | 9/2002 | Yoshimi et al. |
| 6,468,234 B1 | 10/2002 | Van der Loos et al. |
| 6,478,744 B2 | 11/2002 | Mohler |
| 6,485,441 B2 | 11/2002 | Woodward |
| 6,491,647 B1 | 12/2002 | Bridger et al. |
| 6,493,568 B1 | 12/2002 | Bell et al. |
| 6,497,720 B1 * | 12/2002 | Augustine et al. ............. 607/96 |
| 6,498,652 B1 | 12/2002 | Varshneya et al. |
| 6,524,239 B1 | 2/2003 | Reed et al. |
| 6,543,299 B2 | 4/2003 | Taylor |
| 6,546,813 B2 | 4/2003 | Hubbard, Jr. |
| 6,547,743 B2 | 4/2003 | Brydon |
| 6,551,251 B2 | 4/2003 | Zuckerwar et al. |
| 6,551,252 B2 | 4/2003 | Sackner et al. |
| 6,577,897 B1 | 6/2003 | Shurubura et al. |
| 6,585,328 B1 | 7/2003 | Oexman et al. |
| 6,647,289 B2 | 11/2003 | Prutchi |
| 6,684,418 B2 | 2/2004 | Choi |
| 6,685,635 B2 | 2/2004 | Shani et al. |
| 6,721,980 B1 | 4/2004 | Price et al. |
| 6,829,501 B2 | 12/2004 | Nielsen et al. |
| 6,840,117 B2 | 1/2005 | Hubbard, Jr. |
| 6,840,907 B1 | 1/2005 | Brydon |
| 6,921,365 B2 | 7/2005 | Lee |
| 6,932,774 B2 | 8/2005 | Nakatani et al. |
| 7,001,334 B2 | 2/2006 | Reed |
| 7,030,764 B2 | 4/2006 | Smith et al. |
| 7,054,679 B2 | 5/2006 | Hirsh |
| 7,065,396 B2 | 6/2006 | Hampton |
| 7,076,371 B2 | 7/2006 | Fu |
| 7,125,383 B2 | 10/2006 | Hoctor et al. |
| 7,155,273 B2 | 12/2006 | Taylor |
| 7,155,281 B1 | 12/2006 | Fayram |
| 7,173,437 B2 | 2/2007 | Hervieux et al. |
| 7,201,063 B2 | 4/2007 | Taylor |
| 7,204,808 B1 | 4/2007 | Friedman et al. |
| 7,211,053 B2 | 5/2007 | Marmaropou et al. |
| 7,245,956 B2 | 7/2007 | Matthews et al. |
| 7,282,654 B2 | 10/2007 | Salgo et al. |
| 7,319,386 B2 | 1/2008 | Collins, Jr. et al. |
| 7,330,127 B2 | 2/2008 | Price et al. |
| 7,365,031 B2 * | 4/2008 | Swallow et al. ............. 442/181 |
| 7,437,787 B2 | 10/2008 | Bhai |
| 7,459,645 B2 | 12/2008 | Skinner et al. |
| 7,480,953 B2 | 1/2009 | Romano et al. |
| 7,500,280 B2 | 3/2009 | Dixon et al. |
| 7,515,059 B2 | 4/2009 | Price et al. |
| 7,557,718 B2 | 7/2009 | Petrosenko et al. |
| 7,568,246 B2 | 8/2009 | Weismiller et al. |
| 7,631,557 B2 | 12/2009 | DeBeliso et al. |
| 7,646,294 B2 | 1/2010 | Kow et al. |
| 7,656,299 B2 | 2/2010 | Gentry et al. |
| 7,657,956 B2 | 2/2010 | Stacy et al. |
| 7,699,784 B2 | 4/2010 | Fong et al. |
| 2001/0042412 A1 * | 11/2001 | Serban et al. ............. 73/862.46 |
| 2002/0194934 A1 * | 12/2002 | Taylor ...................... 73/862.046 |
| 2003/0004423 A1 | 1/2003 | Lavie et al. |
| 2004/0087865 A1 | 5/2004 | Kelly |
| 2004/0167418 A1 | 8/2004 | Nguyen et al. |
| 2004/0186380 A1 | 9/2004 | Kristiansen |
| 2004/0210155 A1 | 10/2004 | Takemura et al. |
| 2005/0075542 A1 | 4/2005 | Goldreich |
| 2005/0101875 A1 | 5/2005 | Semler et al. |
| 2005/0124864 A1 | 6/2005 | Mack et al. |
| 2005/0171443 A1 | 8/2005 | Gorenberg et al. |
| 2005/0190068 A1 | 9/2005 | Gentry et al. |
| 2005/0241409 A1 * | 11/2005 | Taylor ............................. 73/841 |
| 2005/0245839 A1 | 11/2005 | Stivoric et al. |
| 2005/0268962 A1 * | 12/2005 | Gaudiana et al. ............. 136/255 |
| 2006/0028350 A1 | 2/2006 | Bhai |
| 2006/0065060 A1 | 3/2006 | Ito et al. |
| 2006/0066449 A1 | 3/2006 | Johnson |
| 2006/0100530 A1 | 5/2006 | Kliot et al. |
| 2006/0100534 A1 | 5/2006 | Colombo et al. |
| 2006/0129047 A1 | 6/2006 | Ruotoistenmaki |
| 2006/0173363 A1 | 8/2006 | Felder et al. |
| 2006/0195035 A1 | 8/2006 | Sun |
| 2006/0224072 A1 | 10/2006 | Shennib |
| 2006/0224076 A1 | 10/2006 | Lange et al. |
| 2006/0241510 A1 | 10/2006 | Halperin et al. |
| 2006/0258914 A1 | 11/2006 | Derchak et al. |
| 2006/0260417 A1 * | 11/2006 | Son et al. .................. 73/862.046 |
| 2006/0264767 A1 | 11/2006 | Shennib |
| 2007/0083096 A1 | 4/2007 | Paradiso |
| 2007/0118054 A1 | 5/2007 | Pinhas et al. |
| 2007/0125181 A1 * | 6/2007 | Ofek et al. ....................... 73/778 |
| 2007/0149883 A1 | 6/2007 | Yesha |
| 2007/0156031 A1 | 7/2007 | Sullivan et al. |
| 2008/0200085 A1 * | 8/2008 | Van Bruggen et al. ........ 442/117 |
| 2009/0056027 A1 | 3/2009 | Ball et al. |
| 2009/0093990 A1 | 4/2009 | McGuire et al. |
| 2009/0099480 A1 | 4/2009 | Salgo et al. |
| 2009/0183312 A1 | 7/2009 | Price et al. |
| 2010/0045454 A1 | 2/2010 | Knight et al. |

FOREIGN PATENT DOCUMENTS

| | | |
|---|---|---|
| JP | 2000175904 A | 6/2000 |
| JP | 20000316915 A | 11/2000 |
| JP | 2000000214 | 1/2001 |
| JP | 2001000401 A | 1/2001 |
| JP | 2001037821 A | 2/2001 |
| JP | 2004180804 | 7/2004 |
| JP | 2005013259 | 1/2005 |

| | | |
|---|---|---|
| JP | 2005204930 | 8/2005 |
| JP | 2005218604 | 8/2005 |
| JP | 2008049023 | 3/2008 |
| WO | 2005/000108 | 1/2005 |
| WO | 2009013981 | 1/2009 |

OTHER PUBLICATIONS

Bergen Cable Technology. Cable 101. <Accessed Online> Sep. 7, 2011. <http://www.bergencable.com/technology/technology_cable101.html>.*

J.C. Barbenal et al., "Monitoring the mobility of patients in bed", Medical and Biological Engineering and Computing, pp. 466-468, Sep. 1985.

Charles F. Babbs, et al., "A Pressure-Sensitive Mat for Measuring Contact Pressure Distributions . . .", Biomedical Instrumentation and Technology, pp. 363-370, Sep./Oct. 1990.

Pending U.S. Appl. No. 12/075,937, filed Mar. 13, 2009, which is commonly assigned to the assignee of the present application.

PCT Search Report of the International Searching Authority regarding PCT/US2009/001620, the international counterpart to the present application that includes the same claims as the present application, Oct. 1, 2009.

* cited by examiner

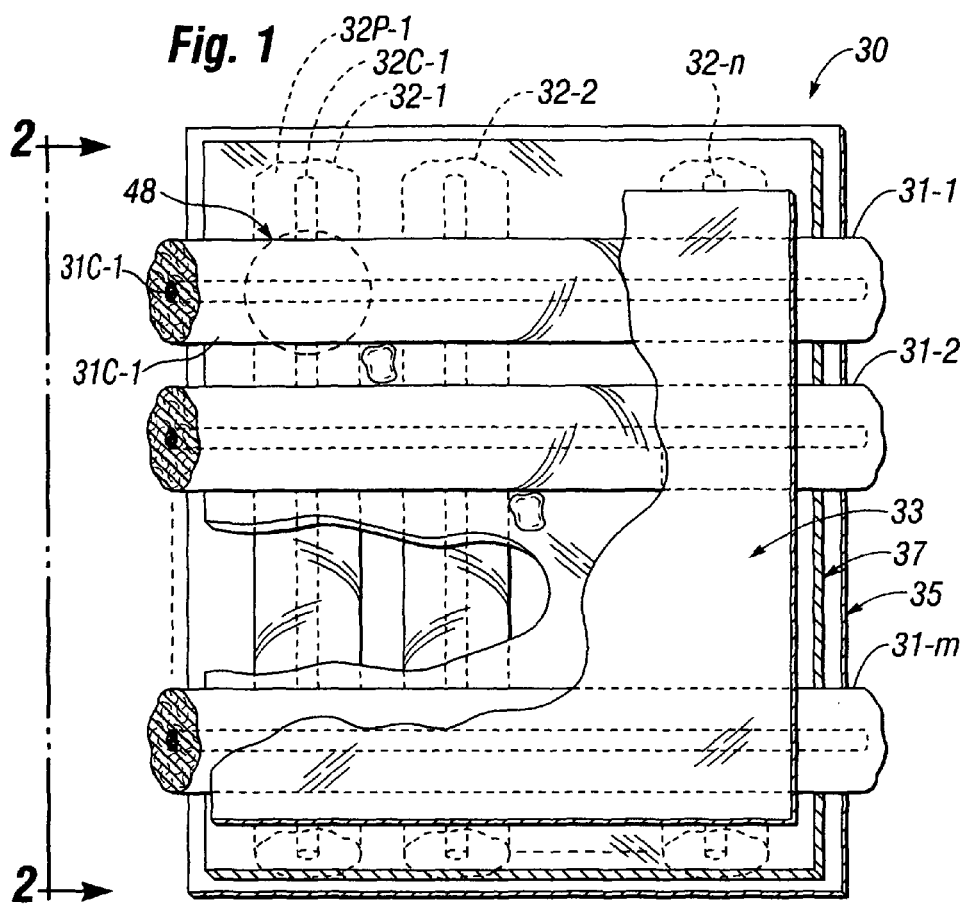
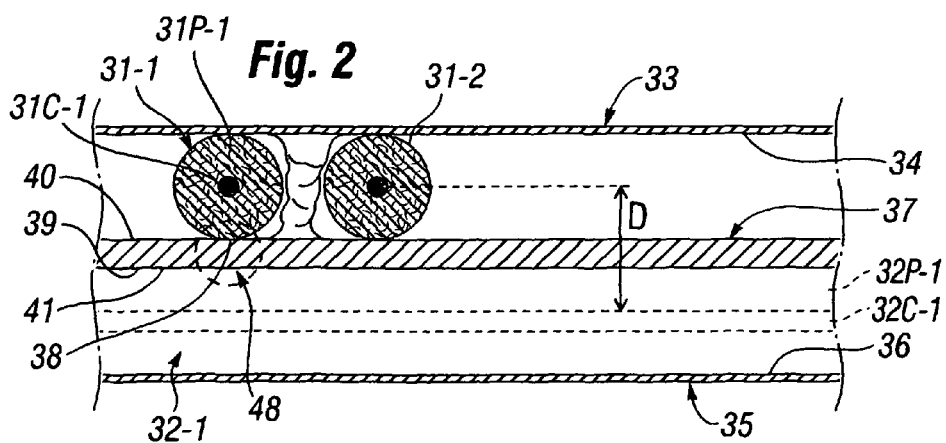

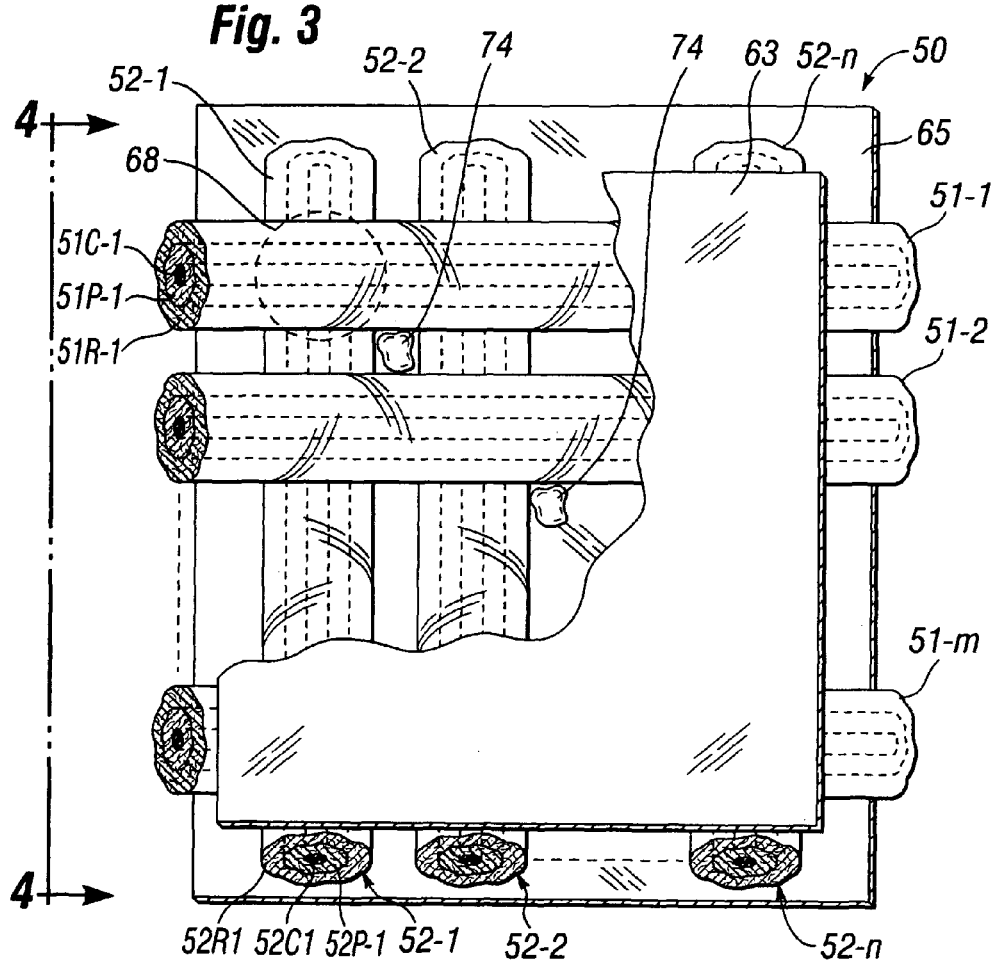
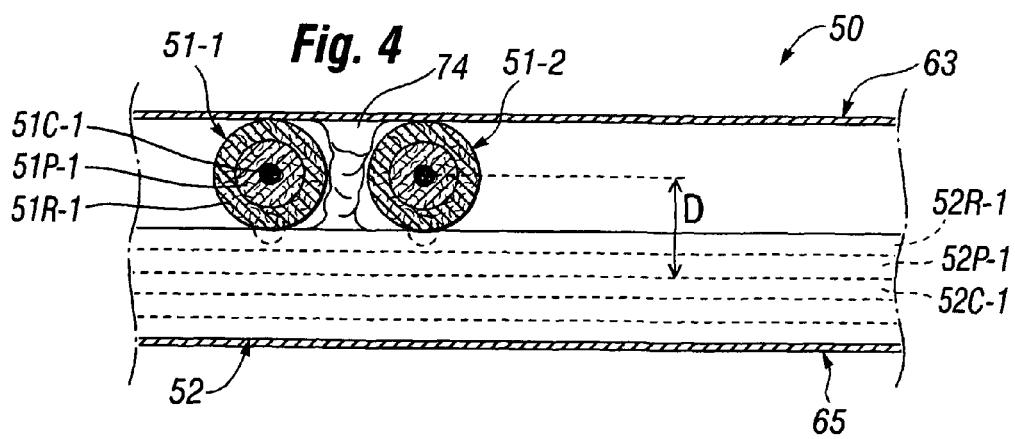

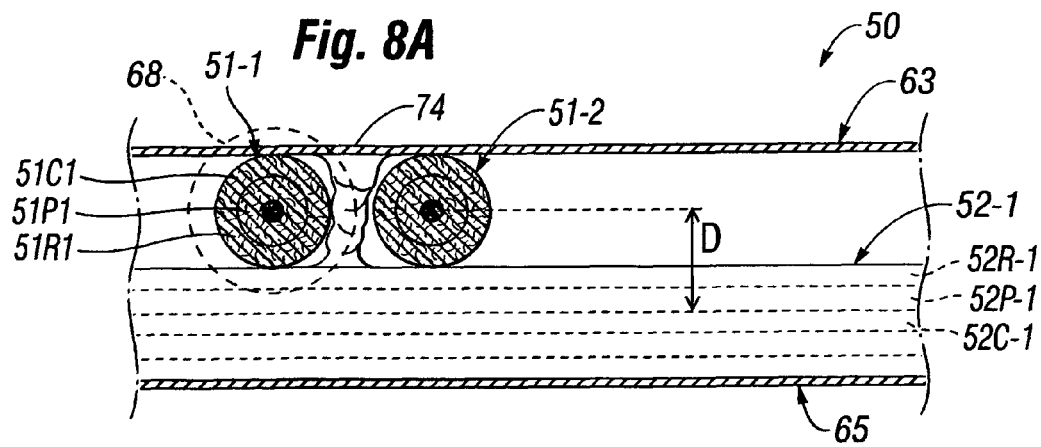
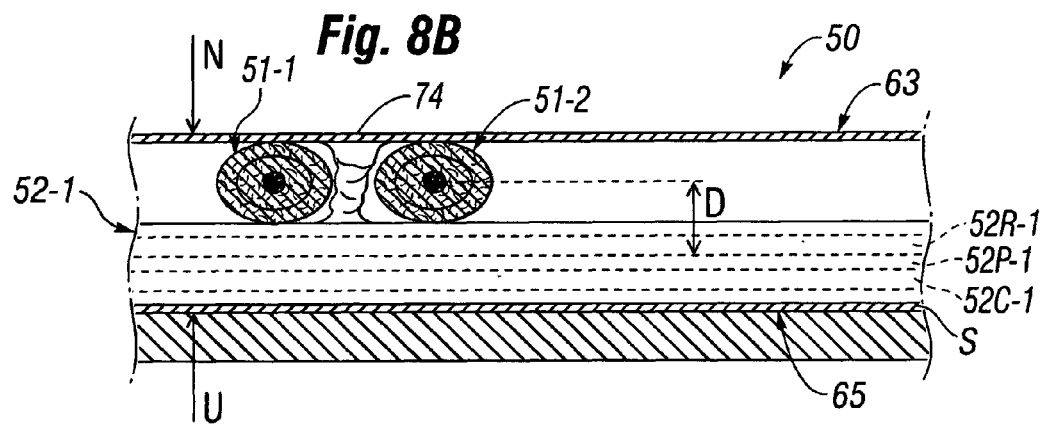
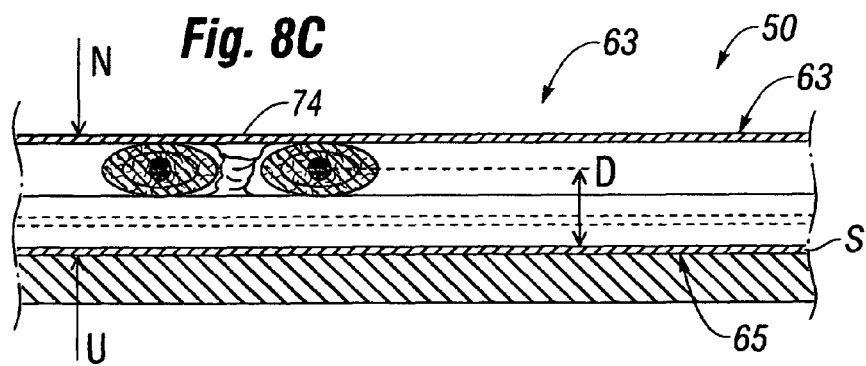

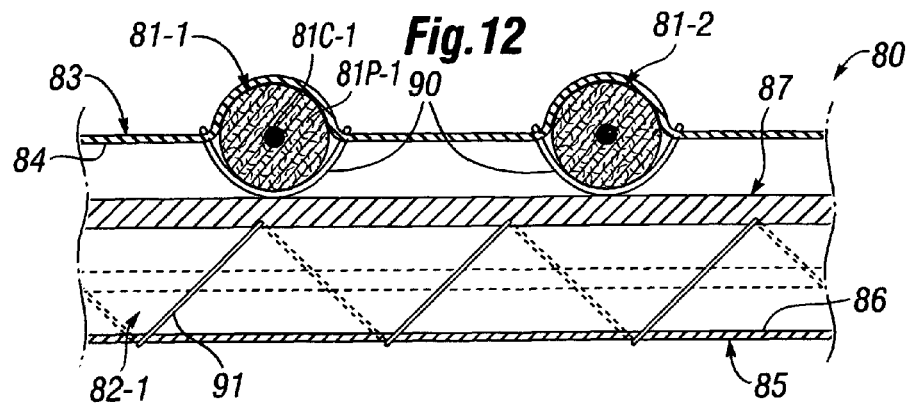
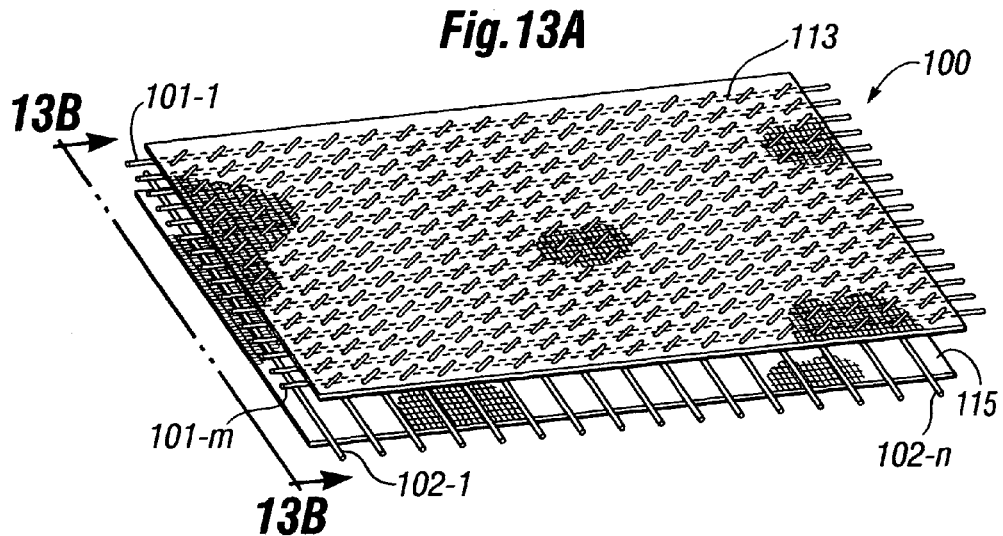
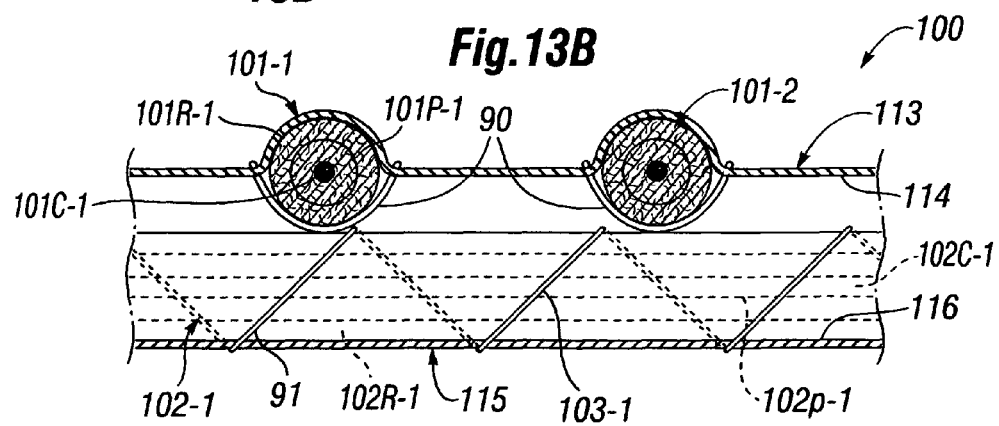

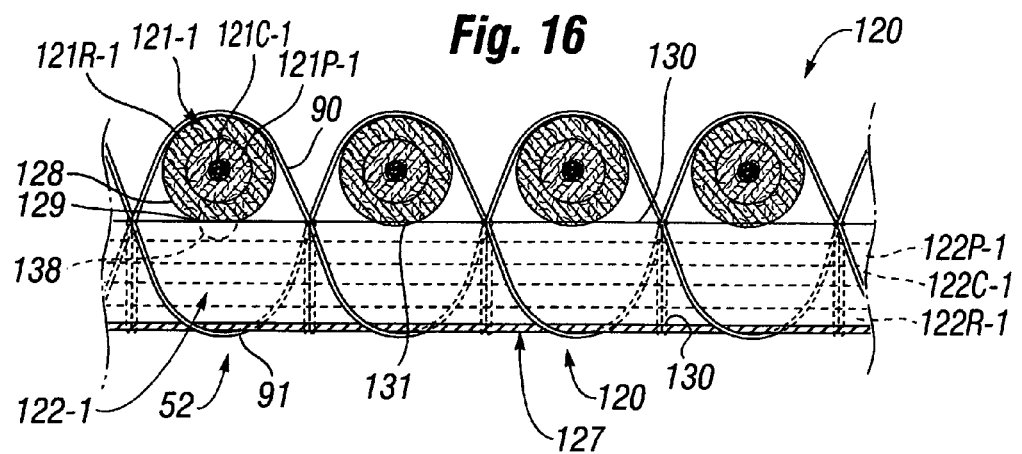
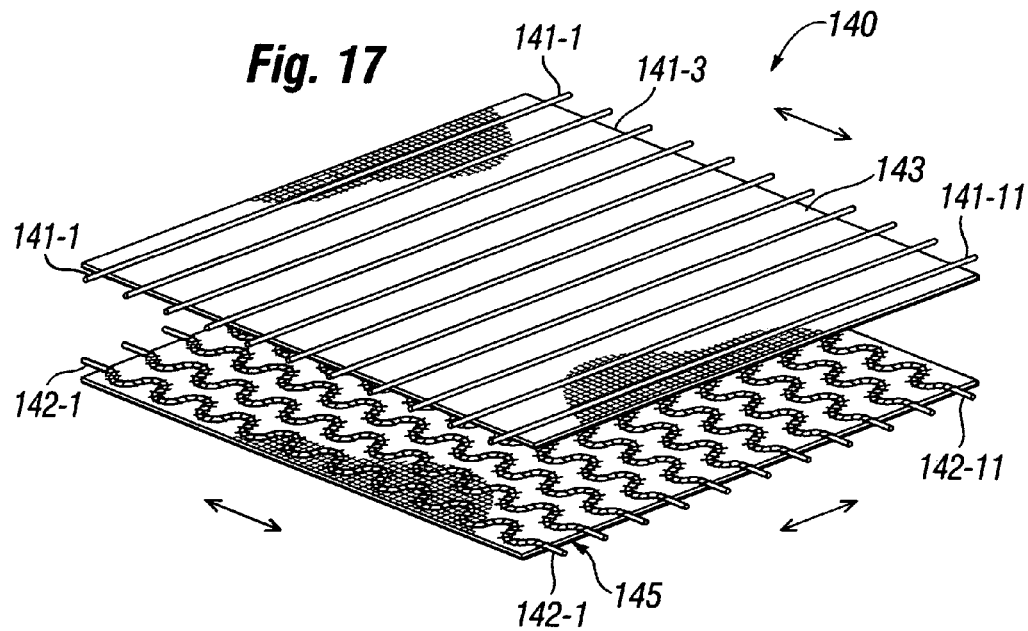

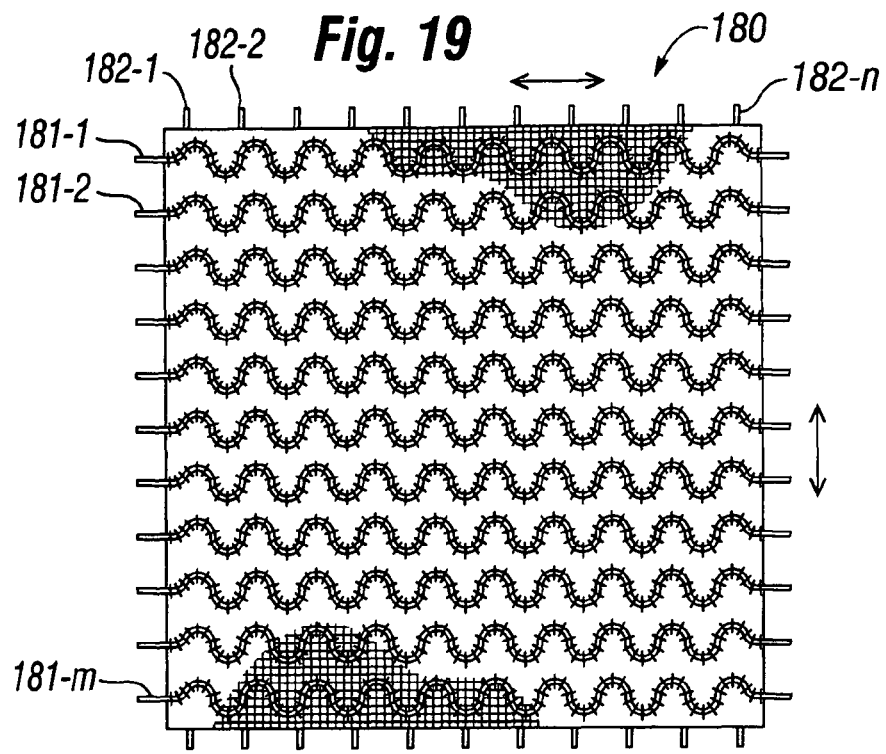
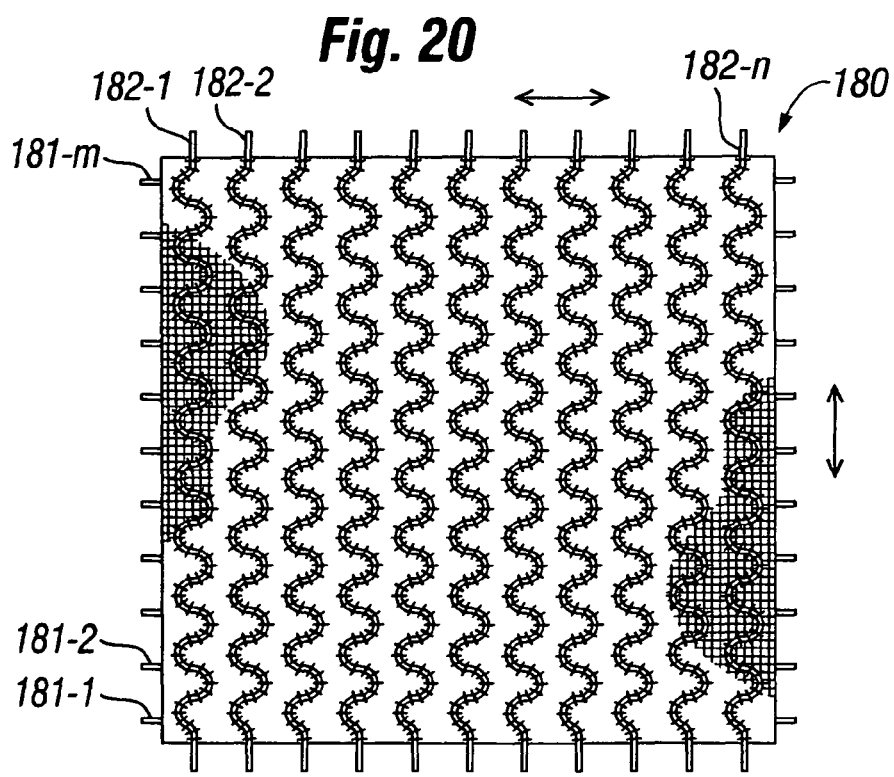

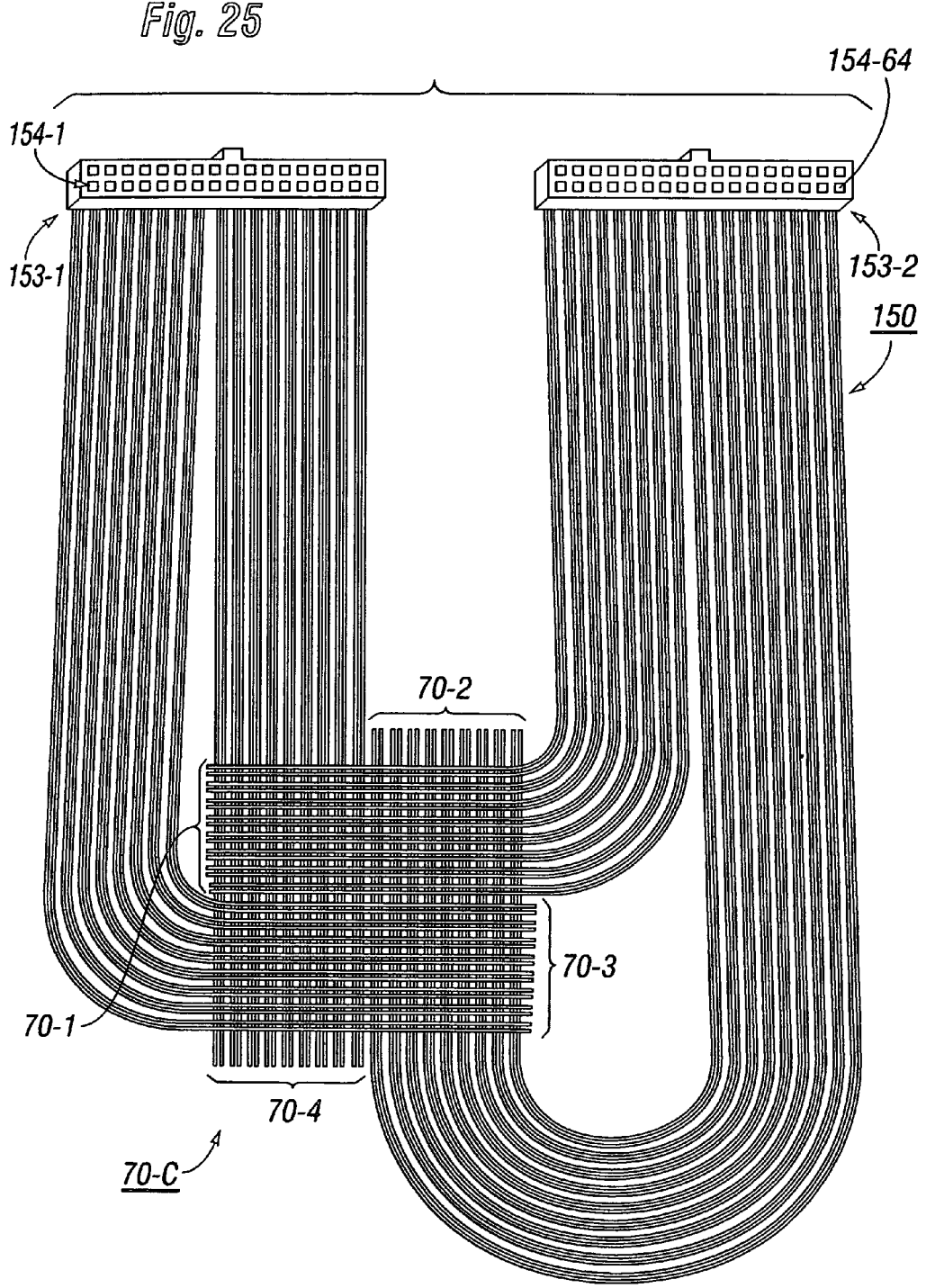

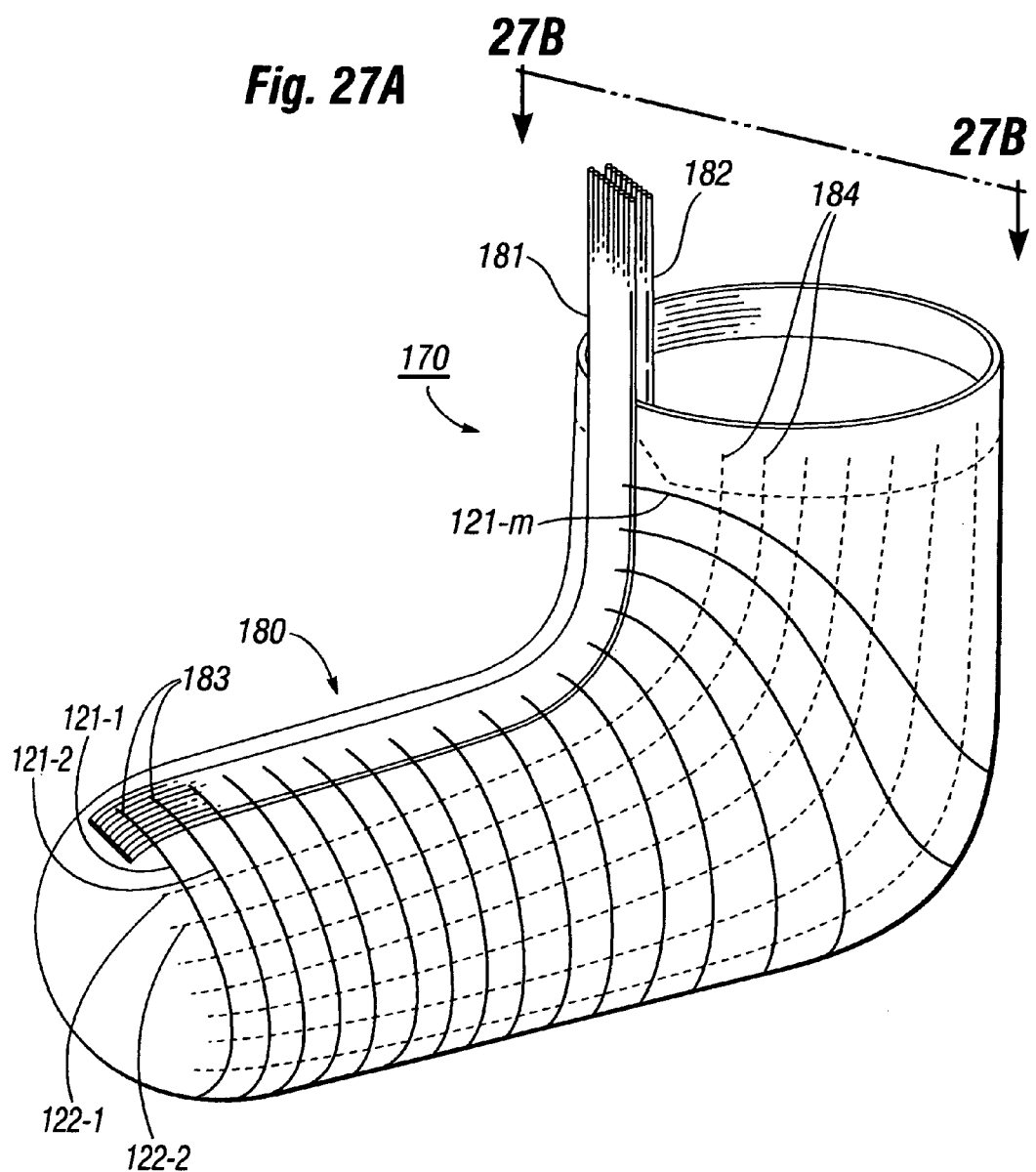

ELASTICALLY STRETCHABLE FABRIC FORCE SENSOR ARRAYS AND METHODS OF MAKING

BACKGROUND OF THE INVENTION

A. Field of the Invention

The present invention relates to transducers or sensors used to measure forces or pressures exerted on a surface. More particularly, the invention relates to fabric force sensor arrays which use elastically stretchable piezoresistive thread sensor elements and are sufficiently conformable to irregularly-shaped objects to be incorporated into clothing wearable by people, and methods of making such arrays.

B. Description of Background Art

Whenever a human body is supported by an object such as a chair or bed, normal and shear forces produced in reaction to the weight of the individual are transmitted from the supporting surface through the skin, adipose tissues, muscles, etc. to the skeleton. The forces exerted on body parts by support surfaces, which are equal and opposite to body weight forces, can in some cases cause damage to tissues. Forces on body parts can compress internal blood vessels and occlude nutrients from the tissue, the product of the magnitude and duration of these forces determining whether tissue damage or morbidity will occur. High pressure alone is generally not sufficient to deleteriously affect tissue. Deep-sea divers for example, are subjected to high, but evenly distributed normal forces and do not suffer from tissue damage. If, however, there is a sufficiently large external pressure gradient on a body part, resulting from, for example, a low-pressure area adjacent to a high-pressure area, internal body fluids can migrate to the area of lower pressure. Tangential or shear forces exerted externally on a body part can also collapse internal capillaries and blood vessels by distorting them along their longitudinal axes. It is therefore extremely important to know both the surface force gradient (pressure gradient) and the externally applied shear force exerted on tissue, because it is the combination of these factors that leads to tissue strain and subsequent tissue death. Thus, even relatively small external shear and normal forces, which may be independent of one another, can combine to produce damagingly large shear stresses on internal tissue. The areas of the human body which are most at risk of developing tissue damage such as a pressure sore are: heel, ischial tuberosities, greater trochanter, occiput and sacrum.

There are available a variety of pressure/force sensors, shear sensors and sensor arrays which are useable for measuring normal and shear forces exerted on human tissues. For example, the present inventor's U.S. Pat. No. 5,751,973, Nov. 5, 1996, Multi-Directional Piezoresistive Shear And Normal Force Sensors For Hospital Mattresses And Seat Cushions discloses thin, planar sensors for measuring reaction forces exerted by mattresses or chair pads on the body of a recumbent or seated patient. One embodiment of the invention disclosed in the specification of the '973 patent includes a sensor comprised of a two-dimensional array of isolated sensor element pads, each consisting of a thin, flat layer formed of a non-conductive elastomeric polymer matrix filled with electrically conductive particles. A matrix of upper and lower conductive elements in electrical contact with upper and lower sides of each sensor pad enables separate measurements to be made of the electrical resistance of each pad. Pressure exerted on each pad, e.g., in response to a normal force exerted on the sensor matrix by a person's body, reduces the thickness of the sensor pad, and therefore its electrical resistance by a bulk or volume piezoresistive effect.

The present inventor also disclosed a novel method and apparatus for measuring pressures exerted on human feet or horses' hooves in U.S. Pat. No. 6,216,545, Apr. 17, 2001, Piezoresistive Foot Pressure Measurement. The novel apparatus disclosed in the '545 patent includes a rectangular array of piezoresistive force sensor elements encapsulated in a thin, flexible polymer package. Each sensor element includes a polymer fabric mesh impregnated with conductive particles suspended in an elastomeric matrix such as silicone rubber. The piezoresistive mesh layer is sandwiched between an array of row and column conductor strip laminations, preferably made of a nylon mesh impregnated with printed metallic paths. Each region of piezoresistive material sandwiched between a row conductor and column conductor comprises an individually addressable normal force or pressure sensor in a rectangular array of sensors, the resistance of which varies inversely in a pre-determined way as a function of pressure exerted on the sensors, and thus enabling the force or pressure distribution exerted by an object contacting the array to be mapped.

In U.S. Pat. No. 6,543,299, Apr. 8, 2003, Pressure Measurement Sensor With Piezoresistive Thread Lattice, the present inventor disclosed a transducer sensor array for measuring forces or pressures exerted on a surface, the array including a fabric-like, two-dimensional lattice of individual force or pressure sensor transducer elements comprising intersecting regions of pairs of elongated, flexible threads, each consisting of a central electrically conductive wire core covered by a layer of piezoresistive material which has an electrical resistivity that varies inversely with pressure exerted on the material.

In U.S. Pat. No. 7,201,063, Apr. 10, 2007, Normal Force Gradient/Shear Force Sensors And Method Of Measuring Internal Biological Tissue Stress, the present inventor disclosed a normal force gradient/shear force sensor device and measurement method for measuring internal stresses in tissues of a person supported by a chair or bed. The device includes a planar matrix array of peripheral normal force sensors radially spaced from central shear force sensors, each including an electrically conductive disk located within a circular opening bordered by circumferentially spaced apart electrodes. The disk and electrodes are located between upper and lower cover sheets made of a stretchable material such as polyurethane, one cover sheet being adhered to the disk and the other sheet being adhered to a support sheet for the electrodes. Motion between the cover sheets in response to shear forces exerted on the array causes the disk to press more or less tightly against the electrodes, thus varying electrical conductance between the disk and electrodes proportionally to the magnitude and direction of the shear force. Each normal force sensor includes an electrically conductive film pressed between row and column conductors. Measurements of conductance values of pairs of sensor, which vary proportionally to normal forces exerted on the sensor, are used to calculate a gradient vector of normal forces exerted by a body part on the sensor array, which is combined with the shear force vectors in an algorithm to calculate internal reaction shear forces, e.g., on flesh near a bony prominence.

In co-pending U.S. patent application Ser. No. 12/075,937, filed Mar. 15, 2008, the present inventor disclosed an Adaptive Cushion Method And Apparatus For Minimizing Force Concentrations On A Human Body. That apparatus included an adaptive cushion for placement on a mattress or chair, the cushion having a matrix of air bladder cells which are individually pressurizable to variable pressures by means of an air compressor and valves. The apparatus disclosed in that application also included a flexible, stretchable planar array of force sensor transducers of novel construction, which is preferably positioned on the upper surface of the cushion, the array having at least one sensor in vertical alignment with each air bladder cell of the cushion.

The sensor array disclosed in the above-cited patent application included stretchable fabric row and column conductors which have sandwiched between inner facing conductive surfaces thereof a stretchable fabric sheet coated with a piezoresistive material. Thus constructed, the planar sensor array is elastically deformable in response to forces exerted on the array by the weight of a human body supported on the upper surface of the sensor array overlying the air bladder cells. Preferably, the sensor array is placed on the upper surfaces of the air bladder cells and maintained in that position by a form-fitting, waterproof, contour sheet. The fabric matrices for both row and column conductors, as well as the central piezoresistive layer, are all made of a material which is elastically deformable in any direction within the plane of the material. In a preferred embodiment, the fabric matrices or the row conductor sheet and column conductor sheet are plated with a copper base coat and nickle cover coat. The central piezoresistive sheet consists of a synthetic fabric matrix coated with piezoresistive coating. The sensor array also has an upper cover sheet which is made of a fabric such as Lycra which has a two-way stretch characteristic, i.e., is elastically stretchable in orthogonal directions.

To avoid cross-talk between measurements of the resistance of individual sensors in the array, by which measurements forces exerted on the sensors are determined, the sensors were constructed in a novel way which gave them non-bilateral, asymmetric current-versus-voltage impedance characteristics. The sensors were modified to have a diode-like characteristic by altering either the upper or lower surface of the central piezoresistive sheet to form thereon a P-N, semiconductor-type junction, by a novel method described in detail in the disclosure of that application.

The flexible force sensor arrays described above have proven highly effective in performing their intended functions. However, there are situations in which it would be desirable to have available force sensor arrays with somewhat different characteristics not offered by prior sensor arrays.

For example, if typical existing flexible sensor arrays are used to measure pressures exerted on a human body by a very form-fitting, conformal wheelchair seat cushion or extremely low pressure bed mattress or cushion, such sensor arrays often interfere with the function of the cushion or bed support surface, and give erroneous force measurements which are used to map the way the bed or chair supports a person. Such errors result from a "hammocking" effect, in which a flexible but not drapable sensor array deployed between fixed support positions cannot conform precisely to the shape of a patient. This effect can occur for example, using sensor arrays that use wire core sensing elements which make the arrays essentially non-stretchable. The lack of conformability of a sensor array alters the way a cushion or bed supports a patient, and also frequently results in forces or pressures exerted on individual sensors in the array being larger than a patient would actually encounter in the absence of the sensor array.

Another situation in which present force sensor arrays for measuring and mapping forces exerted on human body parts are less than satisfactory occurs when attempting to make such measurements in a non-obtrusive, non-interfering manner on body parts which have complex shapes such as the feet.

For example, people who have diabetes often lose feeling sensation in their feet. Since they cannot feel when an ill-fitting shoe is exerting excessive pressure on parts of the foot, the pressure spots can lead to ulcers, which may in turn necessitate amputation of the foot. Accordingly, to prevent such undesirable results, it would be desirable to have a sensor array which could be used to identify such problems, so that corrective actions such as changing the size or shape of a shoe may be taken in a timely manner.

To address the problem of measuring and mapping forces exerted on complex shapes having compound curves, such as a human foot, it would be desirable to have available a sensor array which was similar to clothing fabric in its ability to readily conform to complex, compoundly curved objects such as a human foot. Such sensor arrays could be incorporated into articles of clothing, such as socks. The present invention was conceived of at least partially in response to the unavailability of present sensor arrays to fulfill the requirements described above.

OBJECTS OF THE INVENTION

An object of the present invention is to provide elastically stretchable arrays of force or pressure sensing transducers which are conformable to objects having complex, compoundly curved shapes such as human body parts, to facilitate measuring and mapping forces or pressures exerted on such objects.

Another object of the invention is to provide elastically stretchable fabric-like pressure or force sensor arrays which are sufficiently light in weight and conformally drapable to be incorporated into an article of clothing wearable by a human being.

Another object of the invention is to provide pressure or force sensor arrays which include a matrix of thin, flexible individual force sensors which are incorporated into an elastically stretchable fabric matrix.

Another object of the invention is to provide thin, elastically stretchable drapable planar arrays of piezoresistive force or pressure sensors which are incorporated into a sock or other article of clothing.

Another object of the invention is to provide a thin, elastically stretchable drapable array of piezoresistive force or pressure sensors and an electronic control module electrically coupled to the array which is effective in measuring electrical resistance of individual sensors and thus facilitate mapping of forces or pressures exerted on various parts of the array.

Another object of the invention is to provide a force or pressure measurement system including an elastically stretchable fabric-like array of individual piezoresistive pressure or force sensor elements arranged in a matrix of rows and columns and connected by row and column electrodes to a resistance measurement electronic module, conductive paths to each sensor element including a diode-like circuit element to thus minimize cross talk in the matrix addressing of individual sensors.

Another object of the invention is to provide methods for making elastically stretchable flexible, fabric-like force or pressure sensor arrays using groups of electrically conductive threads arranged into rows and columns.

Another object of the invention is to provide methods for fabricating flexible, elastically stretchable fabric-like force or pressure sensors arranged into X-Y matrices, the sensors including a piezoresistive substance contacted by intersecting conductive threads.

Another object of the invention is to provide methods for fabricating fabric-like force or pressure sensor arrays which include elastically stretchable flexible electrically conductive threads that are coated with a piezoresistive material.

Another object of the invention is to provide methods for fabricating fabric-like force or pressure sensor arrays in which elastically stretchable electrically conductive threads are sewn to a fabric matrix using non-conductive threads.

Another object of the invention is to provide methods for fabricating elastically stretchable electrically conductive threads which have a piezoresistive characteristic.

Another object of the invention is to provide methods for fabricating elastically stretchable piezoresistive conductive threads which have a diode-like, non-bilateral electrical impedance characteristic.

Another object of the invention is to provide elastically stretchable flexible force or pressure sensor arrays which use electrically conductive threads that are elastically stretchable to thereby enhance stretchability of the arrays.

Another object of the invention is to provide elastically stretchable flexible force or pressure sensor arrays which use electrically conductive threads that are sinuously disposed and attached to an elastically stretchable substrate to thereby enhance elastic stretchability of the array.

Various other objects and advantages of the present invention, and its most novel features, will become apparent to those skilled in the art by perusing the accompanying specification, drawings and claims.

It is to be understood that although the invention disclosed herein is fully capable of achieving the objects and providing the advantages described, the characteristics of the invention described herein are merely illustrative of the preferred embodiments. Accordingly, I do not intend that the scope of my exclusive rights and privileges in the invention be limited to details of the embodiments described. I do intend that equivalents, adaptations and modifications of the invention reasonably inferable from the description contained herein be included within the scope of the invention as defined by the appended claims.

SUMMARY OF THE INVENTION

Briefly stated, the present invention comprehends novel pressure or force sensing transducers which include individual force sensing elements that are arranged in planar arrays on or within a substrate consisting of a thin, flexible polymer sheet or a thin sheet of woven or non-woven fabric. Pressure or force sensor arrays according to the present invention utilize elastically stretchable electrically conductive threads which are attached to a thin, elastically flexible substrate sheet consisting of an insulating polymer sheet or fabric sheet using a novel fabrication technique. The arrays are sufficiently flexible, drapable and elastically stretchable to be incorporated into articles of clothing such as socks. This novel construction enables elastically stretchable, conformally drapable pressure or force sensor arrays according to the present invention to be used to measure and map force or pressure distributions on compoundly curved, complexly shaped objects such as a human foot.

Pressure sensor arrays according to the present invention may, for example, be advantageously used to measure and map pressure or force concentrations exerted by an ill-fitting shoe on the foot of a patient who has lost feeling sensations in the foot because of diabetes or other medical ailment. Using information provided by pressure maps producible using the conformable sensor arrays according to the present invention enables re-sizing, modifying or replacing an ill-fitting shoe to reduce pressure concentrations on a patient's foot to values sufficiently low as to preclude the formation of health-threatening ulcers on the foot.

Basic embodiments of elastically stretchable force or pressure sensor arrays according to the present invention utilize flexible, electrically conductive threads having a relatively small diameter, e.g., in a range of about 2 mm to 4 mm. In a basic polymer film substrate version of the invention, each sensor element in an array is formed by the intersection of a first, e.g., upper, row conductive thread attached to the lower surface of an upper thin, insulating polymer substrate sheet, and a second, lower column conductive thread attached to the upper surface of a lower thin, insulating polymer substrate sheet. Preferably, both upper and lower polymer substrate sheets are made of a material which is flexible and elastically stretchable, such as 0.05-0.076 mm thick, elastomeric polyvinyl chloride (PVC).

According to the invention, the intersection of each pair of conductive threads in a sensor array, such as the intersection of a row thread and a column thread, includes sandwiched between the threads a layer, coating, or small dot made of a piezoresistive material, the electrical resistance of which varies inversely with force or pressure exerted on it. Preferably, the piezoresistive material has an elastic or elastomeric characteristic so that cyclical pressure variations on the sensor do not cause excessive hysterisis effects in the electrical resistance versus pressure transfer function of the sensor. A suitable piezoresistive material which meets the foregoing requirements consists of a solid solution of silicone rubber filled with conductive particles such as carbon black or carbon fibers.

When the piezoresistive material between a pair of intersecting conductive threads is compressed as a result of a normal force causing the threads to be urged more closely together, the electrical resistance measured between the pair of conductive threads decreases in proportion to the magnitude of force or pressure. The decrease in resistance is believed to be due to a combination of surface and volume piezoresistive effects.

In the surface piezoresistive effect, the size of the interacting contact area between a pair of conductive threads and a piezoresistive spot increases when the threads are pressed together, thus increasing electrical conductance between the threads. Compression of the elastomeric piezoresistive material apparently increases electrical conductance by a volume piezoresistive effect, a result of conductive particles in the elastomeric matrix of the piezoresistive spot being urged more closely together, and the thickness of the spot being decreased.

According to one aspect of the invention, a basic embodiment of the invention using polymer sheet substrates employs a thin sheet of piezoresistive material sandwiched between upper and lower polymer sheets to which are attached row and column conductive threads, respectively. This embodiment of the invention has three discrete layers.

In a preferred, two-layer embodiment of a polymer film sensor array according to the present invention, piezoresistive material is coated directly onto the outer surfaces of the row conductive threads, the column conductive threads, or, preferably, both row and column conductive threads, thus eliminating the requirement for a third, intermediate substrate sheet containing piezoresistive material In an array of Q individual sensor elements such as those of either of the two basic embodiments of the invention described above, the unambiguous measurement of the resistance of each individual sensor required to unambiguously determine the magnitude of pressure or force exerted on each sensor requires for the Q sensor elements, R=Q+1 lead-out conductors. Thus, each of Q sensor elements may have one terminal of a sensor element connected to a common conductive lead-out conductor, and a separate lead-out conductor connected to an opposite terminal of each sensor element.

For a square matrix of m×n=Q sensors, the number of lead-out conductors required to address each of the Q sensors located at the Q intersection points of m row and n column sensor conductive threads is only R=2√Q. Thus, for example, in an array of 64 sensor elements, individually measuring the resistance of each of the sensor elements would require 65 electrically isolated lead-out conductors. On the other hand, using a matrix addressing arrangement, there would only be required a total of 16 lead-out conductors, i.e., 8 row conductors and 8 row column conductors. Therefore, it would be desirable to utilize matrix addressing to measure the resistance of each sensor element.

There is, however, a problem associated with measuring the resistance of sensor elements in an array using matrix addressing of the sensor elements. The problem results from the fact that the electrical resistances of all the non-addressed sensor elements in an array shunts the resistance of each addressed sensor element, resulting in cross-talk inaccuracies in measurements of individual sensor element resistances, and therefore of pressures inferred from those measurements.

To overcome the cross-talk problem, sensors according to the present invention are preferably fabricated to have an asymmetric, diode-like current-versus-voltage transfer function. The diode-like transfer function is achieved by treating the piezoresistive coatings on the surface of the conductive threads to form thereon a P-N junction. Alternatively, either or both upper and lower surfaces of a piezoresistive film between row and column conductive threads is treated to give it a P-N junction characteristic. As explained in detail below, the P-N junction characteristic is provided by depositing an electroless coating containing an oxide of copper or other metal to a surface of a piezoresistive, carbon-containing layer.

Preferred embodiments of pressure sensor arrays according to the present invention are preferably fabricated using sheets of a woven elastic fabric, rather than sheets of polymer film. The woven fabric results in sensor arrays which are more stretchable and drapable, and hence more readily conformable to irregularly curved surfaces.

In a basic embodiment of a force sensor array using a woven fabric substrate according to the present invention, laterally spaced apart, longitudinally disposed conductive threads are fastened to the lower surface of a first, upper fabric sheet. Preferably, the conductor threads are fastened to the upper fabric substrate sheet by sewed, zig-zag stitching using non-conductive threads of smaller diameter than the conductive threads.

A second, lower fabric substrate sheet is prepared in the same way as the upper sheet, with the conductive threads located on the upper side of the lower sheet.

Upper and lower sheets may optionally be fabricated from a single substrate fabric sheet that has conductive threads sewn onto one surface thereof, the sheet cut in two and one of the halves reversed and rotated 90 degrees so that confronting surfaces of the two half sheets form a matrix of intersections, consisting of rows of conductive threads and columns of conductive threads. A piezoresistive film layer is then positioned between upper and lower fabric substrate sheets, and the three sheets fastened together along their peripheral edges to thus form a two-dimensional planar array containing a matrix of individual sensor elements.

In preferred embodiments of force sensor arrays using fabric substrates according to the present invention, the piezoresistive film layer positioned between row and column conductive threads of the sensor consists of coatings of a piezoresistive substance which are applied to outer surfaces of the conductive threads. The piezoresistive coating may be applied to the outer surface of row or column conductors by a novel process according to the invention, but is preferably applied to both row and column threads.

Sensor arrays having the novel construction according to the present invention which use highly flexible, elastically stretchable row and column conductor threads stitched to the inner facing surface of a pair of confronting substrate panels made of a light-weight drapable fabric are readily conformable to irregular surfaces, thus facilitating measurement of forces exerted on surfaces of irregularly shaped objects.

Preferred embodiments of fabric substrate piezoresistive force sensor arrays according to the present invention are given an enhanced stretchability, drapability and conformability by utilizing a stretchable fabric which contains Spandex or Lycra as the substrate material. Preferably, the stretchable fabric substrates have an isotropic, or at least two-way stretch characteristic, so that the sensor array may be elastically stretched to conform to an irregularly shaped object with equal compliance in all directions, or at least two perpendicular directions, respectively. With this construction, the conductive threads themselves may limit stretchability of the sensor array. The stretchability and conformability of sensor arrays according to the present invention is preferably increased by either of the following two methods.

According to a first method of enhancing stretchability of sensor arrays according to the present invention, stretchability of an array is increased by using a stretchy conductive yarn rather than a monofilament thread for the row and column conductive threads. The conductive yarn may be used as a core for either row or column piezoresistive threads, but is preferably used for both row and column conductor threads, to provide enhanced two-way stretchability.

In a second method of enhancing stretchability of sensor arrays according to the present invention, either or both row and column piezoresistive threads are arranged in a serpentine or sinuously disposed lines with respect to a straight base line between opposite ends of a row or column thread, rather than remaining on the base lines. With this sinuous arrangement, the slack formed by transversely disposed portions of a conductive thread enables the longitudinal spacing between peaks and valleys of the sinuously curved thread to increase when the fabric is stretched in the direction of the thread base line, and decrease when the fabric relaxes to an unstretched state. Put another way, the spatial wavelength of the sinuously curved conductive thread increases when the sensor array is elastically stretched, and decreases when stretching forces on the array are relaxed to thus allow the array to elastically recover its unstretched shape.

Optionally, sensor arrays according to the present invention may utilize both stretchy elastic conductive threads, and sinuously curved arrangements of the threads, to maximize elastic stretchability of the arrays.

According to another aspect of the invention, a single layer fabric substrate sensor array is provided which is light in weight and highly conformable. This embodiment of sensor arrays according to the present invention uses a single fabric substrate panel which has been impregnated with a piezoresistive substances. Row and column conductive threads are sewn to opposite outer surfaces of the fabric substrate. Enhanced stretchability and conformability for this embodiment may optionally be provided by using either or both stretchy yearn and sinuously curving of the conductive threads, as described above.

BRIEF DESCRIPTION OF THE DRAWINGS

FIG. 1 is a partly broken away perspective view of a basic embodiment of a three-layer piezoresistive thread pressure sensor array according to the present invention, which uses a pair of polymer film outer substrates and a central piezoresistive layer.

FIG. 2 is a vertical transverse sectional view or end view of the sensor array of FIG. 1 taken in the direction 2-2.

FIG. 3 is a partly broken-away, upper perspective view of a second, two-layer embodiment of a piezoresistive thread pressure sensor array according to the invention, in which the central piezoresistive layer shown in the basic embodiment of FIGS. 1 and 2 is replaced by a piezoresistive coating on conductive threads of the sensor array.

FIG. 4 is a vertical transverse sectional or end view of the sensor array of FIG. 3, taken in the direction 4-4.

FIG. 8A is a fragmentary transverse sectional view of the sensor array of FIGS. 3 and 4 on a further enlarged scale, showing the disposition of row and column piezoresistive threads to form force sensing elements, with no external force applied to the array.

FIG. 8B is a view similar to that of FIG. 8A, but with a moderate normal force applied to the sensor elements.

FIG. 8C shows the sensor element with a larger external force applied thereto.

FIG. 12 is a vertical transverse sectional view, of the sensor array of FIG. 9, taken in the direction 12-12.

FIG. 13A is a partly broken-away, exploded upper perspective view of a fourth, two-layer piezoresistive thread pressure sensor array using fabric substrates, according to the invention, in which the central piezoresistive layer of the embodiment shown in FIG. 9 is replaced by a piezoresistive coating on conductive threads of the sensor array.

FIG. 13B is a vertical transverse sectional view of the sensor array of FIG. 13A, taken in the direction 13B-13B.

FIG. 16 is a vertical transverse sectional view of the sensor array of FIG. 14, taken in the direction 16-16.

FIG. 17 is partly broken-away, exploded upper perspective view of a modification of the fabric substrate sensor arrays of FIG. 9, 13 or 14 in which lower column conductive threads of the sensor array are disposed in a sinuous arrangement on the fabric lower substrate panel.

FIG. 19 is an upper plan view of the sensor array of FIG. 18.

FIG. 20 is a lower plan view of the sensor array of FIG. 18.

FIG. 25 is an upper perspective view of a force measuring sensor apparatus using two-layer sensor arrays of the type shown in FIG. 5.

FIG. 27A is a perspective view of a sock incorporating the sensory array of FIG. 14-16 or 17-20.

DESCRIPTION OF THE PREFERRED EMBODIMENTS

Figure 5:
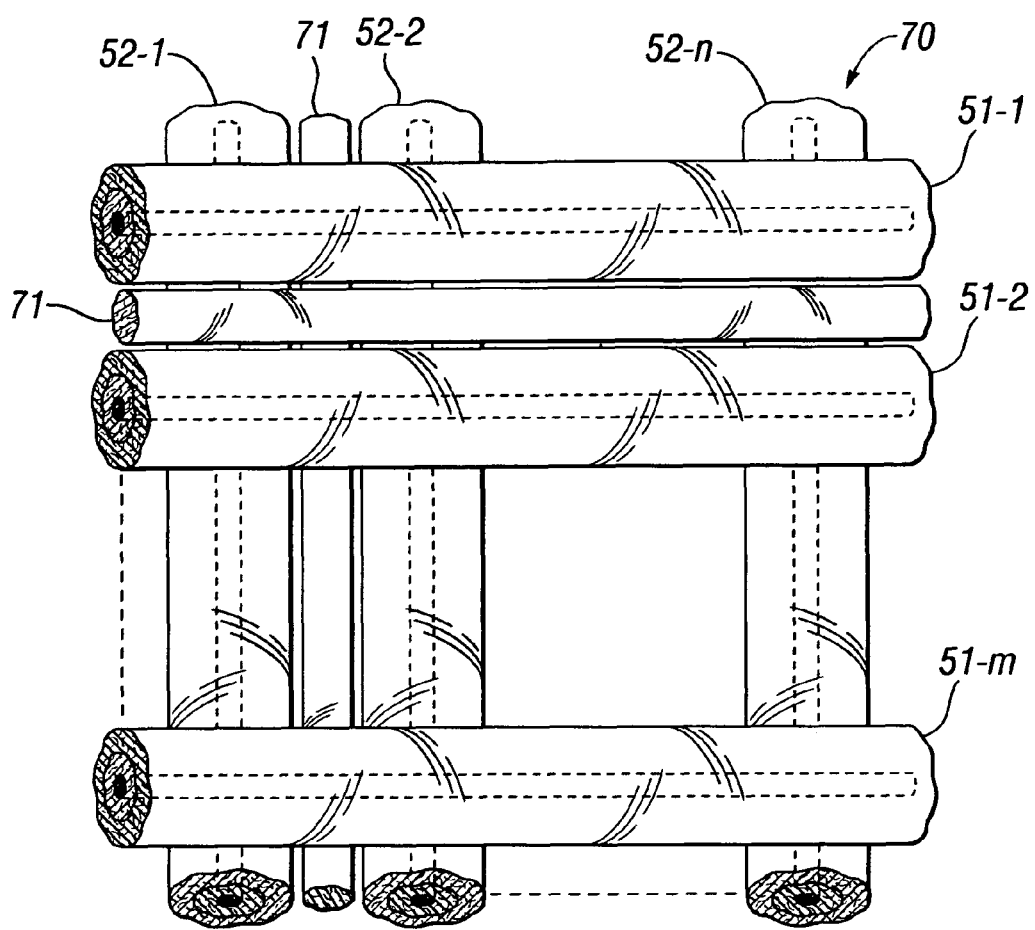
FIG. 5 is a fragmentary perspective view of a modification of the sensor array of FIGS. 1 and 3 in which adjacent pairs of more closely packed row and column conductor threads are spatially and electrically isolated from each other by non-conductive threads.
Figure 6:
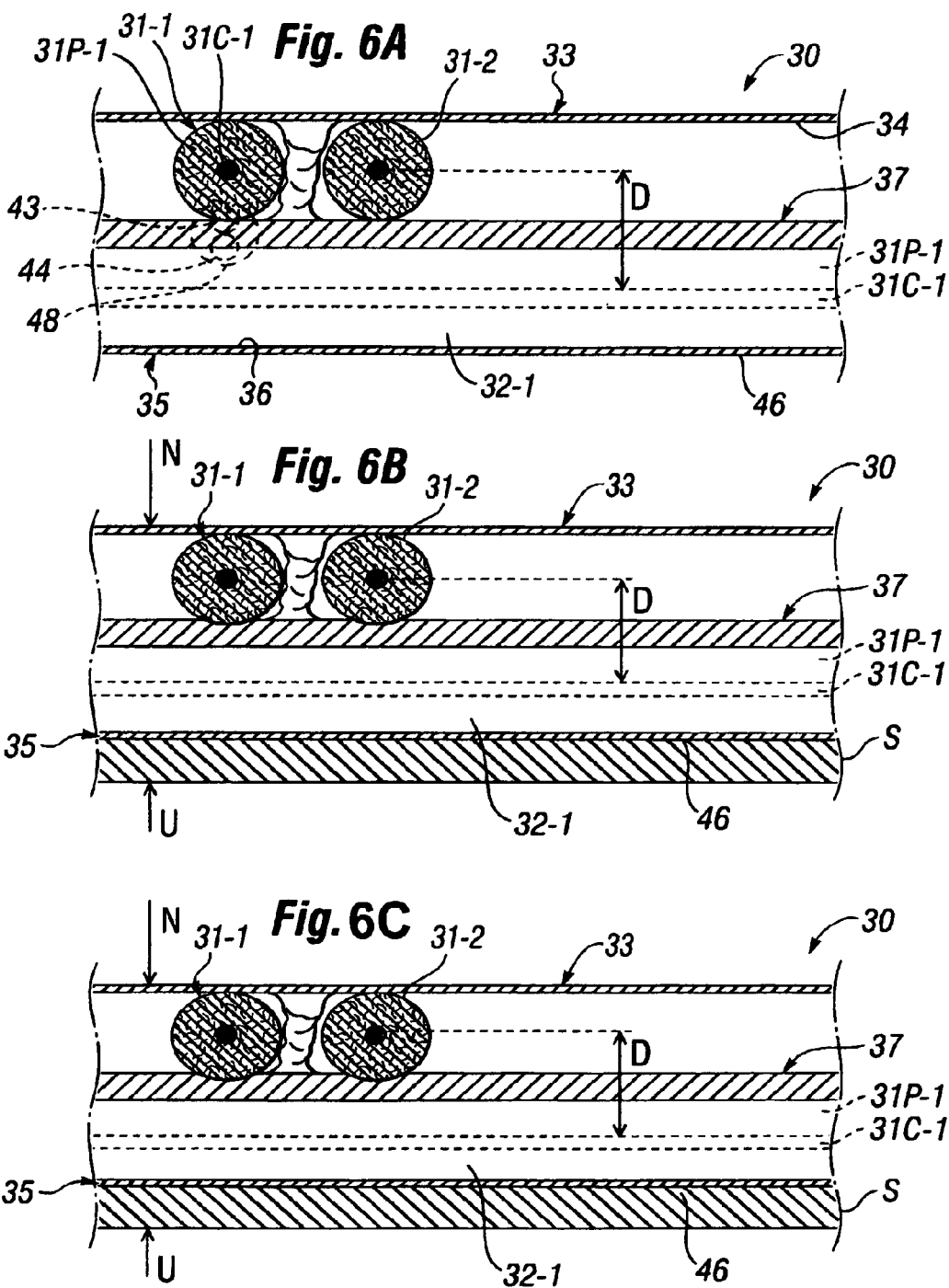
FIG. 6A is a fragmentary transverse sectional view of the sensor array of FIGS. 1 and 2, on a further enlarged scale, showing the disposition of crossed row and column conductive threads contacting a central piezoresistive layer to form force sensing elements, with no external force applied to the elements.
FIG. 6B is a view similar to that of FIG. 6A, but with a moderate normal force applied to the sensor elements.
FIG. 6C shows the sensor elements with a larger external force applied thereto.

The entire disclosure of U.S. Pat. No. 6,543,299 is hereby incorporated by reference into the present disclosure.

FIGS. 1-34 illustrate various aspects of elastically stretchable, conformable fabric force sensor arrays, and methods for making the arrays, according to the present invention.

Referring first to FIGS. 1 and 2, a first, basic, three-layer embodiment of a force sensor array according to the present invention is shown.

As shown in FIGS. 1 and 2, a three-layer force sensor array 30 according to the present invention includes a plurality m of elongated, straight thin conductive row threads 31-*l* through 31-*m* and a plurality n of elongated, straight thin, conductive column threads 32-*l* through 32-*n*.

According to the invention, the electrically conductive row threads 31 and column threads 32 consist of an elastically stretchable monofilament or woven polymer core 31C, 32C, which has been treated to make the threads electrically conductive, as by silver plating the core to form coatings 31P, 32P on cores 31C, 32C, respectively.

One type of example embodiment of a sensor array 30 according to the present invention used row and column conductive threads 31, 32 made from silver plated nylon thread, 117/17 2 ply, catalog #A264, obtained from LESS EMF, 809 Madison Avenue, Albany, N.Y. 12208, USA. That conductive thread had a lineal resistivity of about 75 ohms per foot, and an elastic stretchability of about 1 percent, i.e., at least 10 times greater than that of a stainless steel wire of a similar diameter.

A second type of example embodiment of a sensor array according to the present invention uses row and column conductive threads made from silver plated stretchy nylon yarn, that plated yarn having the designation Shieldex,®Lycra dtex 20, obtained from W.Zimmerman, GmbH & Co. K6, Riederstrasse 7, D-88171, Weiter-Simmerberg, Germany. That conductive thread had a lineal resistivity of about 500 ohms per foot. The elastic stretchability of that conductive yarn is greater than 30 percent, i.e., at least 300 times greater than that of a stainless steel wire of a similar diameter.

As shown in FIGS. 1 and 2, a row threads 31 and column threads 32 lie in parallel planes but are inclined with respect to one another, such as at an angle of ninety-degrees. In the example embodiment 30, row conductive threads 31 are fastened to the lower surface 34 on an upper substrate sheet 33, and column conductive threads 32 are fastened to the upper surface 36 of a lower substrate sheet 35.

As may be seen best by referring to FIG. 2, sensor array 30 includes a thin central lamination or sheet 37 made of a piezoresistive material. As shown in FIG. 2, opposed inner facing outer surfaces 38, 39 of row and column conductive threads tangentially contact upper and lower surfaces 40, 41, respectively, of central piezoresistive sheet 37. Thus, as shown in FIGS. 1 and 2, each crossing point or intersection of a row conductive thread 31 and a column conductive thread 32 forms a piezoresistive sensor element 48 which consists of a small portion of central piezoresistive sheet 37 that is electrically conductively contacted by a row conductive thread and a column conductive thread.

In example embodiments of sensor array 32, piezoresistive sheet 37 was fabricated by coating a stretchy," i.e., elastically stretchable thin Lycra-like fabric sheet with a piezoresistive material. A suitable fabric sheet, which forms a matrix for supporting the piezoresistive material, was a fabric known by the trade name Platinum, Milliken, Style #247579, obtained from the manufacturer, Milliken & Company, Spartenburg, S.C., USA. That fabric had a fiber content of 69 percent nylon and 31 percent Spandex, a thread count of about 88 threads per inch, and aa thickness of 0.010 inch.

The piezoresistive material used to coat the fabric matrix is made as follows:

A solution of graphite, carbon powder, nickel powder and acrylic binder are mixed in proportions as required to obtain the desired resistance and piezoresistive properties. Silver coated nickel flake is used to achieve force response in the low force range of 0 to 1 psi, graphite is used for the mid range of 1 to 5 psi and Charcoal Lamp Black is used for high force range of 5 to 1000 psi. Following is a description of the substances which are constituents of the piezoresistive material:

Silver Coated Nickel Flake:
Platelets approximately one micron thick and 5 microns in diameter.
Screen Analysis (−325 Mesh) 95%.
Apparent Density 2.8.
Microtrac d50/microns 12-17.
Available from: Novamet Specialty Products Corporation, 681 Lawlins Road, Wyckoff, N.J. 07481
Graphite Powder:
Synthetic graphite, AC-4722T
Available from: Anachemia Science
4-214 DeBaets Street
Winnipeg, MB R2J 3W6
Charcoal Lamp Black Powder:
Anachemia Part number AC-2155
Available from: Anachemia Science
4-214 DeBaets Street
Winnipeg, MB R2J 3W6
Acrylic Binder:
Staticide Acrylic High Performance Floor Finish
P/N 4000-1 Ph 8.4 to 9.0
Available from: Static Specialties Co. Ltd.
1371-4 Church Street
Bohemia, N.Y. 11716

Following are examples of mixtures used to make piezoresistive materials having different sensitivities:

Example I for forces in the range of 0 to 30 psi:
200 ml of acrylic binder
10 ml of nickel flake powder
10 ml of graphite powder
20 ml of carbon black
Example II for forces in the range of 0-100 psi
200 ml of acrylic binder
5 ml of nickel flake powder
5 ml of graphite powder
30 ml of carbon black
Example III for forces in the range of 0-1000 psi
200 ml of acrylic binder
1 ml of nickel flake powder
1 ml of graphite powder
40 ml of carbon black The fabric matrix for piezoresistive sheet 37 is submerged in the piezoresistive coating mixture. Excess material is rolled off and the sheet is hung and allowed to air dry.

According to the invention, upper and lower substrate sheets 33, 34 are made of a thin, flexible insulating material, such as 0.002 inch thick polyurethane or polyvinyl chloride (PVC). Preferably, the substrate sheets 33, 34 are made of an elastomeric material which has a relatively high degree of elastic stretchability, so that sensor array 30 is readily stretchable and conformable to the surface of an irregularly-shaped object. It can be appreciated, however, that conductive threads 31, 32 should also be elastically stretchable to facilitate stretchability of sensor array 30. This is because conductive threads 31, 32 are affixed to substrate sheet 33, 34, respectively, by, for example, blobs of adhesive 42, as shown in FIG. 2. Piezoresistive sheet 37 is also fixed to upper and lower substrate sheets 33, 34 by blobs of glue 42.

FIGS. 6A-6C illustrate how the arrangement of row and column conductive threads 31, 32, in combination with central piezoresistive layer 37 of sensor array 30 shown in FIGS.

1 and 2, form individual force sensing elements 48. Each force sensor element 48 is located at the cross-over or intersection point 49 of a row conductive thread, e.g., 31-1, 31-2, . . . 31-m, with a column conductive thread, e.g., 32-1, 32-2, . . . 32-n, for a M×N matrix of sensor elements. Thus, individual sensor elements may be identified by the nomenclature 48-XXX-YYY, where XXX denotes row number and YYY denotes column number.

As shown in FIGS. 2 and 6A, with no external force applied to sensor array 30, at each cross-over point 49 of a row conductive thread 31 and a column conductive thread 32 of sensor array 30, there is an upper electrically conductive tangential contact region 43 between central piezoresistive layer 37 and the upper conductive row thread, and a lower electrically conductive tangential contact region 44 between the piezoresistive layer and the lower, column conductive thread.

With no external force applied to sensor array 30, the electrical resistance between a row conductive thread 31 and column conductive thread 32, which consists of the series resistance of upper contact region 43, lower contact region 44, and the effective resistance of piezoresistive material 45 of piezoresistive layer 37 between the upper and lower contact regions is relatively high. The relatively high resistance results from the fact that in this case, tangential contact regions 43 and 44 are relatively small, and the thickness of uncompressed piezoresistive volume 45 is at its maximum value. However, as shown in FIGS. 6B and 6C, when sensor array 30 is placed on a supporting surface S and a normal force N of increasing magnitude is applied to upper surface 47 of the sensor array 30, the electrical resistance between a row conductive thread 31 and a column conductive thread 32 decreases, as will now be described.

Referring still to FIGS. 2 and 6A, it may be seen that with no external force applied to sensor array 30, tangential contact regions 43, 44 between row and column conductive threads 31, 32 and central piezoresistive layer 37 are relatively small, since the threads have a circular outer cross-sectional shape, which tangentially contacts flat planar surfaces of the piezoresistive layer. Under these circumstances, the small sizes of contact regions 43, 44 results in relatively high electrical resistance between central piezoresistive layer 37 and row and column conductive threads 31, 32. Moreover, with central piezoresistive layer 37 uncompressed, its thickness and hence resistance are at a maximum value.

FIGS. 6B and 6C illustrate the effects of increasing external normal forces or pressures exerted on sensor array 30. As shown in FIGS. 6B and 6C, sensor array 30 is placed with its lower surface 46 supported on a surface S and a force N is exerted perpendicularly downwards on upper surface 47 of the array, resulting in a reaction force U being exerted upwardly by supporting surface S on lower surface 46 of the array. Since central piezoresistive layer 37 is resiliently deformable, the compressive force on it decreases the thickness T of the part of the layer between a row conductive thread 31 and a column conductive thread 32. This reduction in path length through piezoresistive layer 37 between a row conductive thread 31 and a column conductive thread 32 causes the electrical resistance R between the threads to decrease in value.

Figure 7:
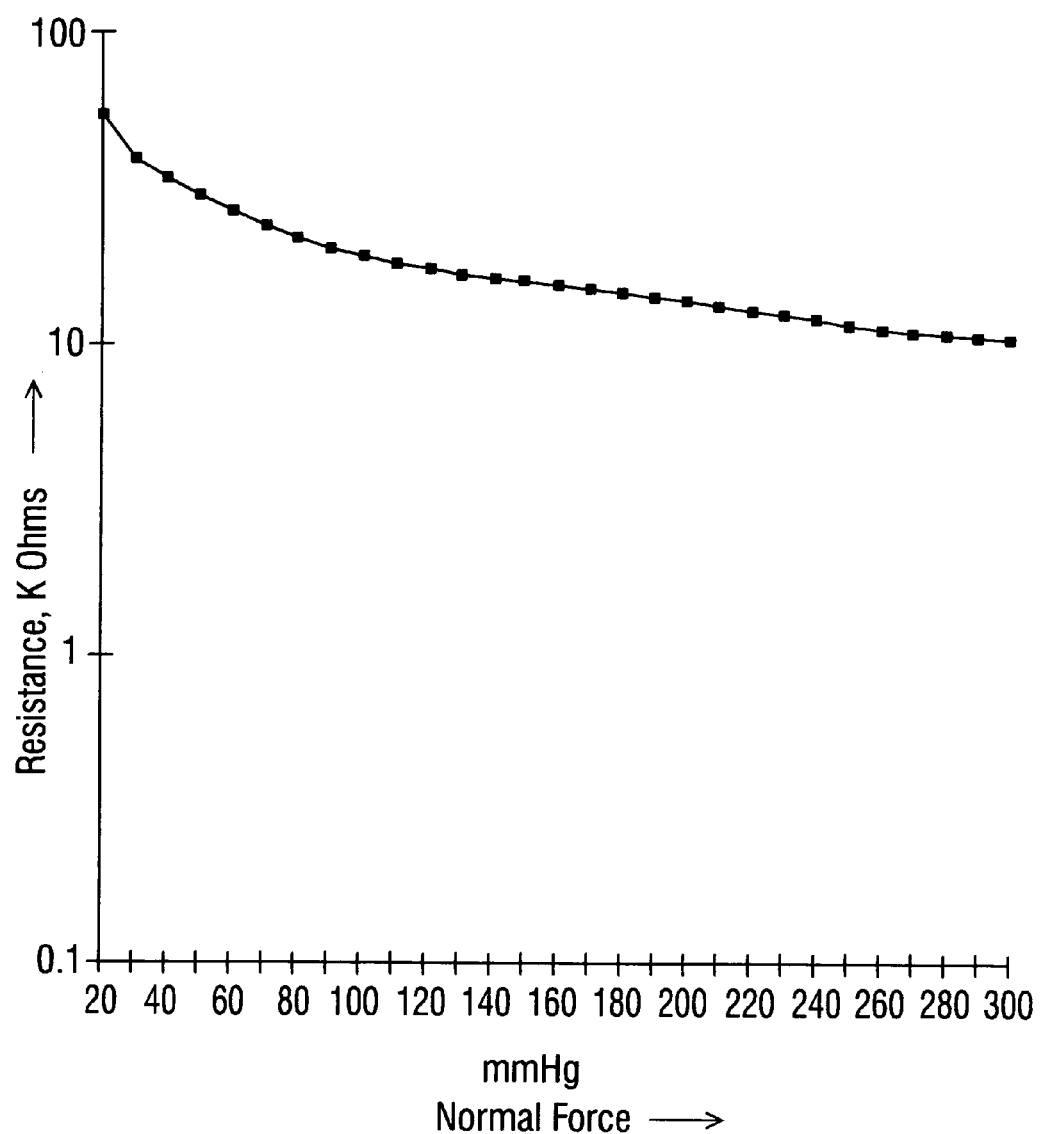
FIG. 7 is a graph showing electrical resistance plotted as a function of force or pressure exerted on sensor elements of the sensor arrays shown in FIGS. 1 and 3.

For moderate values of normal force N, as shown in FIG. 6B, resilient deformation of central piezoresistive layer 37 is relatively small, resulting in a relative small reduction in electrical resistance R between the threads. Larger forces N exerted on sensor array 30 cause a larger deformation of the central piezoresistive layer, as shown in FIG. 6C, resulting in a larger percentage reduction in resistance R. FIG. 7 illustrates in a general way the reduction in electrical resistance measurable between a row conductive thread 31 and a column conductive thread 32, as a function of normal force or pressure exerted on array 30 at these points.

FIGS. 3 and 4 illustrate another embodiment 50 of a piezoresistive thread pressure sensor array according to the present invention, in which the central piezoresistive layer shown in FIGS. 1 and 2 and described above is replaced by a piezoresistive coating on either, or preferably both, row conductive threads 51 and column conductive threads 52.

Sensor array 50 is facially similar to sensor array 20 disclosed and shown in FIGS. 1 and 2 of U.S. Pat. No. 6,543,299, but differs from that sensor array in important ways. Thus, row and column piezoresistive threads 51, 52 of sensor array 50 are made of elastically stretchable polymer cores 51C, 52C which have been treated by silver plating the cores to form on the threads electrically conductive coatings 51P, 52P, respectively. The coatings on either or both cores 51C, 52C are clad with a layer 51R, 52R, respectively, of a material which has a piezoresistive characteristic. According to the invention, the piezoresistive material used to form cladding layers 51R, 52R on plated surfaces 51P, 52P of cores 51C, 52C of piezoresistive conductive threads 51, 52 may have a composition similar to that described above for making piezoresistive sheet layer 37.

A method for making piezoresistive sensor threads by cladding conductive threads with a layer of a piezoresistive material according to the present invention includes preparing a slurry of piezoresistive material having a composition described in examples 1, 2 and 3 above. A highly conductive polymer thread, such as silver plated nylon thread 117/17 2 play, Cat #124 available from LESS EMF Inc., 804 Madison Avenue, Albany, N.Y. 12208, is then immersed in a container holding the slurry, for a period of about 10 seconds. The end of a thread which has been immersed is withdrawn from the container, and while it is still wet, drawn through a circular aperture through a scraper plate.

In an example embodiment, a conductive thread having a core diameter of 0.25 mm and wet-coated diameter in the range of about 0.4 mm to 0.5 mm was drawn through a #360 scraper having a diameter of 0.45 mm, thus resulting in a wet scraped diameter of about 0.45 mm. The scraped thread was then fed through a stream of air heated to a temperature of 70 degrees C. at a linear travel speed of 100 mm/minute for a period of 5 minutes, to thus form a solidified coating having a diameter of about 0.4 mm.

As shown in FIGS. 3 and 4, piezoresistive row and column threads 51, 52 are fastened to upper and lower substrate sheets 63, 65, by suitable means such as adhesive blobs 74. Substrate sheets 63, 64 are made of a thin, flexible material such as 0.003 inch thick elastomeric polyurethane or polyvinyl chloride (PVC) that has a relatively high degree of elasticity.

FIGS. 3 and 8A-8C illustrate how the arrangement of row and column piezoresistive threads 51, 52 of sensor array 50 form individual force sensing elements 69. In response to progressively larger compressive normal forces, piezoresistive cladding layers 51R, 52R on row and column conductive core threads 51C, 52C are progressively compressed into oval cross-sectional shapes of smaller diameter. Thus, as shown in FIGS. 8A-8C, the electrical resistance of each sensor element 70 decreases in inverse proportion to applied pressure, as shown in FIG. 7.

FIG. 5 illustrates a modification 70 of the sensor arrays shown in FIGS. 1 and 3 and described above. Modified sensor array 70 may alternatively employ the three-layer construction of sensor array 30 shown in FIG. 1, or the two-layer construction of sensor array 50 shown in FIG. 3. The modification consists of fabricating sensor array 70 with electrically insulating material between adjacent rows and/or columns of conductive threads. Thus, for example, the modification 70 of two-layer sensor 50 shown in FIG. 3 includes elongated insulating threads 71, made for example of 0.012 inch diameter polyester disposed between each pair of adjacent row conductive threads 51 and each pair of adjacent column conductive threads 52.

The insulating threads 71 are secured in place by any suitable means, such as adhesively bonding the threads to substrate sheets 63, 65 (see FIGS. 2 and 4). This constructing enables sensor array 70 to be substantially wrinkled or otherwise deformed to conform to an irregularly shaped surface, without the possibility of pairs adjacent row or column conductive threads 51 or 52 contacting one another to thus cause an electrical short circuit which would result in erroneous sensor element resistance measurements and force determinations. Optionally, insulation between adjacent pairs of row and column conductive threads could be applied by lightly spraying an aerosol insulation acrylic paint to hold the conductive threads in place.

FIGS. 9-12 illustrate a three-layer embodiment 80 of a piezoresistive thread force sensor array according to the present invention. Sensor array 80 is similar to the basic embodiment 30 of sensor array shown in FIGS. 1-2 and described above. However, sensor array 80 uses upper and lower substrate sheets 83, 85 which are made of woven fabric rather than polymer films. This construction, in conjunction with the use of stretchy conductive row and column threads 81, 82 made of plated nylon or Lycra cores, results in a sensor array that is even more flexible, elastically stretchable and drapable than sensor array 30.

Figure 10:
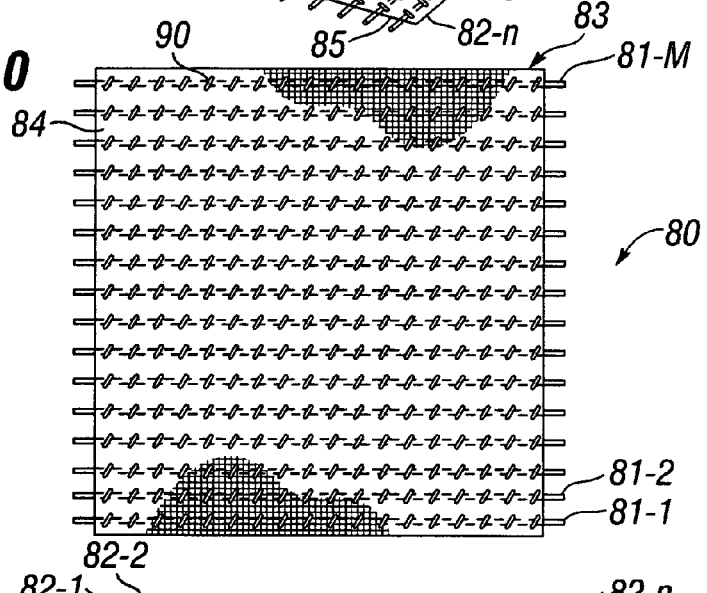
FIG. 10 is a fragmentary view of the sensor array of FIG. 9 on an enlarged scale and showing a lower plan view of an upper, horizontal row conductor part of the sensor array.

As may be seen best by referring to FIG. 10, sensor array 80 includes a plurality of parallel, laterally spaced apart conductive row threads 81 which are fastened to the lower surface 84 of upper fabric substrate sheet 83. The row conductive threads 81 are fastened to lower surface 84 of upper substrate sheet 83 by any suitable means. In a preferred embodiment, as shown in FIG. 10, each row conductive thread 81 is fastened to a substrate sheet by sewing the thread to fabric substrate sheet 83 by a smaller diameter, non-conductive thread 90 arranged in an elongated zig-zag stitching pattern. In an example embodiment, threads 90 consisted of 0.005-0.010 inch diameter, 100% polyester woven thread. For greater strength required for sensor arrays used to measure larger forces, threads 90 may optionally be monofilaments.

In an example embodiment of a sensor array 80 according to the present invention, upper and lower substrate sheets 83, 85 were made from a light-weight, elastically stretchable fabric, both of the two following fabrics were tested and found suitable for substrate sheets 83, 85. (1) Milliken "Millglass" brand, Style #247579, composed of 69% nylon, 31% spandex, and having a weight of 1.8 oz./sq. yd. (2) Milliken "Interlude" brand, product #247211, composed of 82% nylon, 18% Lycra, and having a weight of 3.2-3.4 oz. Per sq. yd. Both of the foregoing fabrics are available from Miliken & Company, 23 Fiddler's Way, Lafayette, N.J. 07848.

Figure 11:
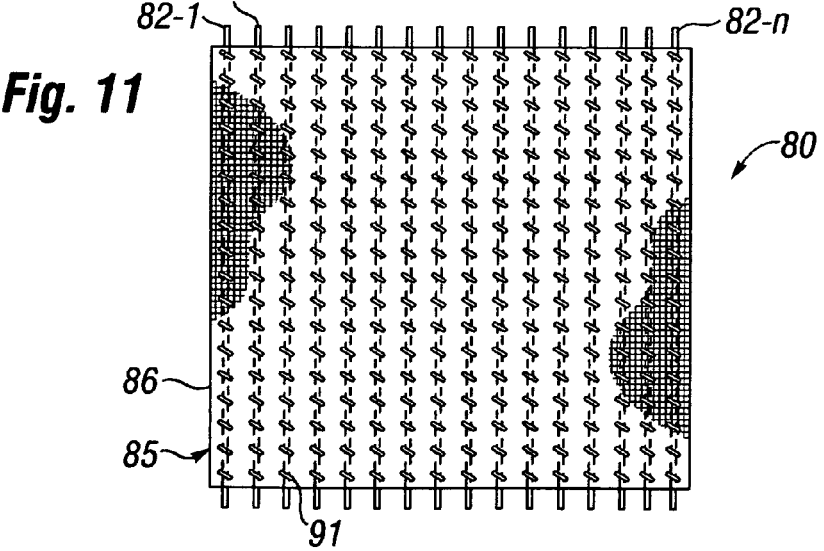
FIG. 11 is a fragmentary view of the sensor array of FIG. 9, on an enlarged scale and showing an upper plan view of a lower, vertical column conductor part of the sensor array.

As shown in FIG. 11, lower column conductive threads 82 are fastened to the upper surface 86 of lower fabric substrate sheet 85 by non-conductive threads 91 of the same type as non-conductive threads 90 and in the same zig-zag stitching manner.

Figure 9:
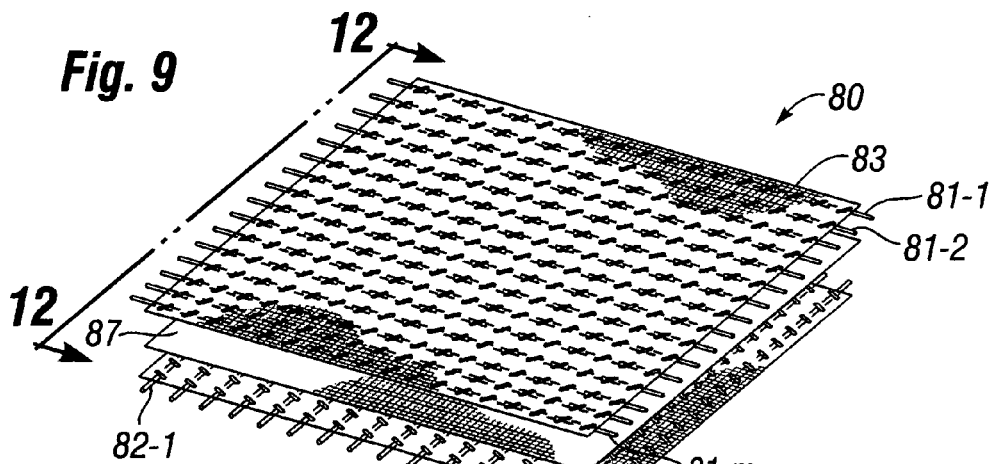
FIG. 9 is a partly broken-away perspective view of a third, three-layer embodiment of a piezoresistive threads pressure sensor array according to the invention, which uses a pair of fabric outer substrates and a central piezoresistive layer.

As shown in FIGS. 9 and 12, three-layer fabric substrate sensor array 80 includes a central piezoresistive sheet 87, which may have a composition and construction similar to that of central piezoresistive sheet 37 of sensor array 30 described above.

As may be seen best by referring to FIG. 13B, upper, row piezoresistive threads 101 are attached to lower surface 114 of upper fabric substrate sheet 113 by insulating sewn threads 90 arranged in zig-zag stitches. Similarly, lower, column piezoresistive threads 102 are attached to the upper surface 116 of lower substrate sheet 115 by sewn threads 91 arranged in zig-zag stitches.

FIGS. 13A and 13B illustrate another two-layer embodiment 100 of a piezoresistive thread force sensor array according to the present invention. Sensor array 100 is similar to sensor array 80. However, in sensor array 100, conductive row and column threads 81, 82 are replaced by piezoresistive threads 101, 102 which have the same characteristics as piezoresistive threads 51, 52 of the two-layer polymer film substrate sensor array 50 shown in FIGS. 3 and 4 and described above. This construction eliminates the requirement for the central piezoresistive sheet 87 of three-layer fabric sensor array 80 described above.

Figure 14:
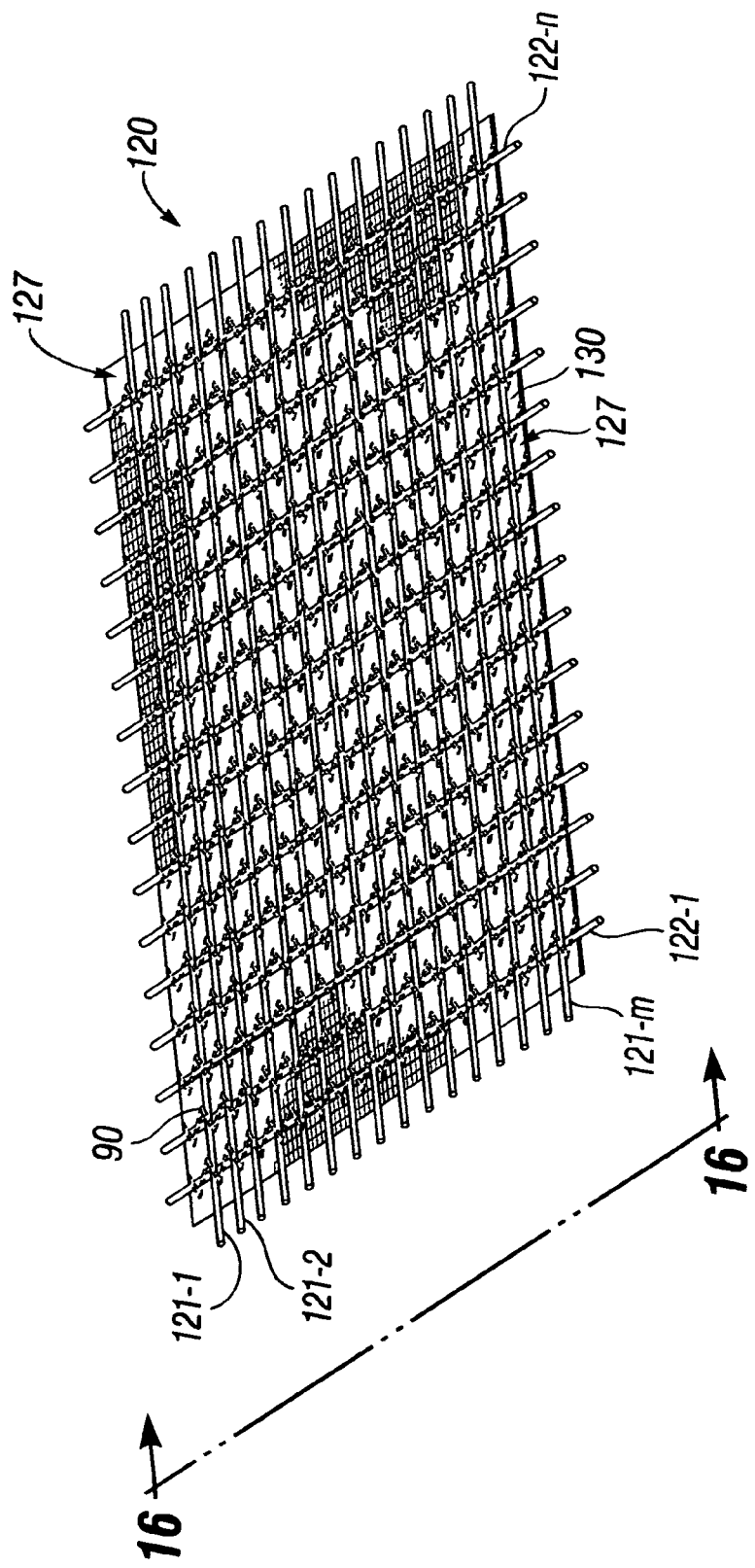
FIG. 14 is a partly broken-away upper perspective view of a fifth, single layer embodiment of a piezoresistive thread pressure sensor array according to the invention which has a single fabric substrate, in which both row and column piezoresistive threads are fastened to the same side of a single insulating substrate sheet.
Figure 15:
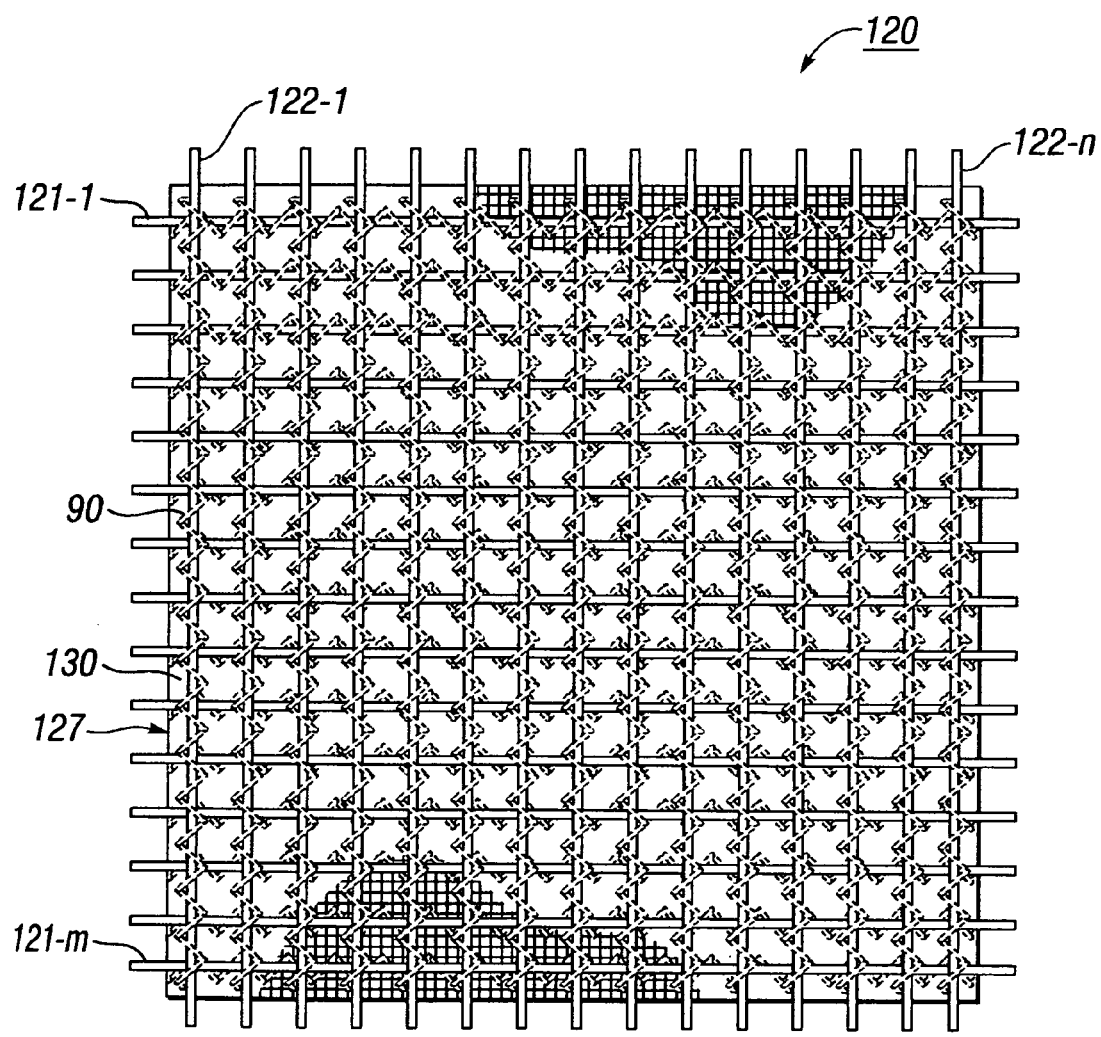
FIG. 15 is an upper plan view of the sensor array of FIG. 14.
Figure 18:
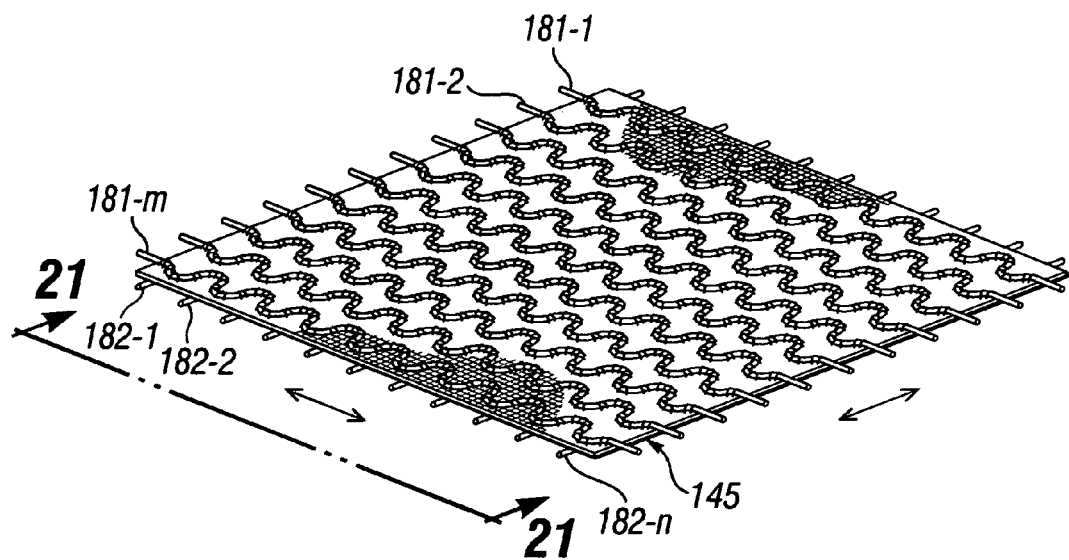
FIG. 18 is an upper perspective view of another modification of the single layer fabric substrate sensor array of FIG. 14 in which both the row and column conductive threads are sinuously arranged and located on opposite sides of a piezoresistive substrate sheet.

FIGS. 14-16 illustrate a fifth, single layer embodiment 120 of a force sensor array in which row and column piezoresistive threads are attached to a single side of a single insulating fabric substrate sheet 127.

As shown in FIGS. 14-16, single layer fabric force sensor array 120 has a single substrate sheet 127 which is made from a light-weight, elastically stretchable fabric. Both of the two following fabric were listed and found suitable for making substrate sheet 127. (1) Milliken "Millglass" brand, Style #247579, composed of 69% nylon, 31% spandex, and having a weight of 1.8 oz./sq. yd., and (2) Milliken "Interlude" brand, product #247211, composed of 82% nylon, 18% Lycra, and having a weight of 3.2-3.4 oz. Per sq. yd. Both of the foregoing fabrics are available from Milliken & Company.

A plurality of parallel, laterally spaced apart column piezoresistive threads 122 are fastened to the upper surface 130 of the substrate sheet. The column piezoresistive threads are made from silver-plated nylon thread, Catalog #A-264 obtained from LESS EMF, or preferably from silver-plated stretchy nylon yarn, both of which are described in detail above in conjunction with the description of sensor array 30.

In a preferred embodiment of single fabric substrate sheet sensor array 120, each column piezoresistive thread 122 is fastened to substrate sheet 127 by a smaller diameter, non-conductive thread 91 arranged in an elongated zig-zag stitching pattern. In an example embodiment, threads 91 consisted of 0.005-0.010 diameter, 100% polyester.

As shown in FIGS. 14, 15 and 16, sensor array 120 includes a plurality of parallel, laterally spaced apart piezoresistive row threads 121 which are also fastened to the upper surface 130 of substrate sheet 127. As shown in FIG. 16, m row piezoresistive threads 121 are fastened to substrate sheet 127 by non-conductive threads 90 of the same type as threads 91 and in the same zig-zag stitching manner.

As shown in FIG. 16, opposed inner facing outer surface 128, 129 of row and column piezoresistive threads 121, 122 tangentially contact each other. Thus, as shown in FIGS. 14-16, each crossing of a row piezoresistive thread 121 with a column piezoresistive thread 122 forms a piezoresistive sensor element 138 which consists of a small portion of piezoresistive coatings of a row and column piezoresistive thread tangentially contacting one another.

FIG. 17 illustrates a modification of the force sensor arrays using fabric substrate sheets shown in FIG. 9, 13 or 14 and described above. As shown in FIG. 17, a lower fabric substrate sheet 145 of modified force sensor array 140 has attached thereto lower, column conductive piezoresistive threads 142 which are sinuously curved with respect to parallel straight base lines between opposite ends of each thread, rather than lying directly on the base lines, as are the column conductive threads 82 of sensor array 80 shown in FIG. 11. With this arrangement, lower fabric substrate sheet 145 is even more readily elastically stretchable in directions parallel to the column thread base lines because longitudinally spaced apart points on the fabric substrate sheet are not constrained to be at maximum lengths by the less elastically stretchable conductive threads. Thus, the stretchability of the column substrate sheet 145 is limited only by its intrinsic stretchability since the arrangement of column conductive threads 142 allows them to conform readily to size of the substrate sheet by changing spacing between peaks and valleys of the sinuously curved conductive threads, i.e., altering the spatial wavelengths of the sinuous curves formed by threads.

Optionally, upper row piezoresistive threads 141 may also be sinuously arranged in the same manner as lower column piezoresistive threads shown in FIG. 17, to thus enhance elastic compliance, or stretchability, of sensor array 140 is in directions parallel to the row conductive threads as well as in directions .parallel to the column piezoresistive threads. Also, either or both row and column conductive threads of three-layer sensor arrays such as those of the type shown in FIG. 1 may be sinuously arranged to provide enhanced uniaxial or biaxial stretchability.

FIGS. 18-21 illustrate another modification 180 of the single fabric substrate sheet sensor array 120 of FIG. 14. Sensor array 180 has upper, row conductive threads 181 and lower, column conductive threads 182 which are both sinuously arranged on opposite sides of a fabric piezoresistive central substrate sheet 187. This construction gives array 180 greater elasticity in directions parallel to the column conductive threads 182 as well as in directions parallel to row conductive threads 181.

Figure 21:
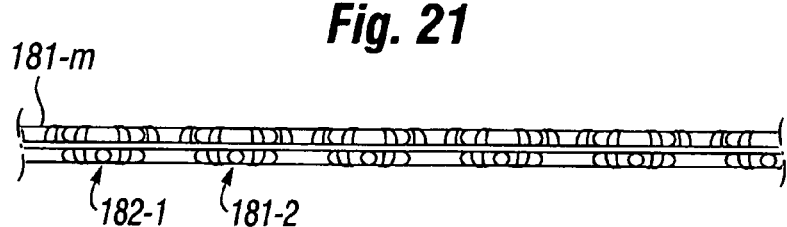
FIG. 21 is a vertical transverse sectional view of the sensor array of FIG. 19
Figure 21A:
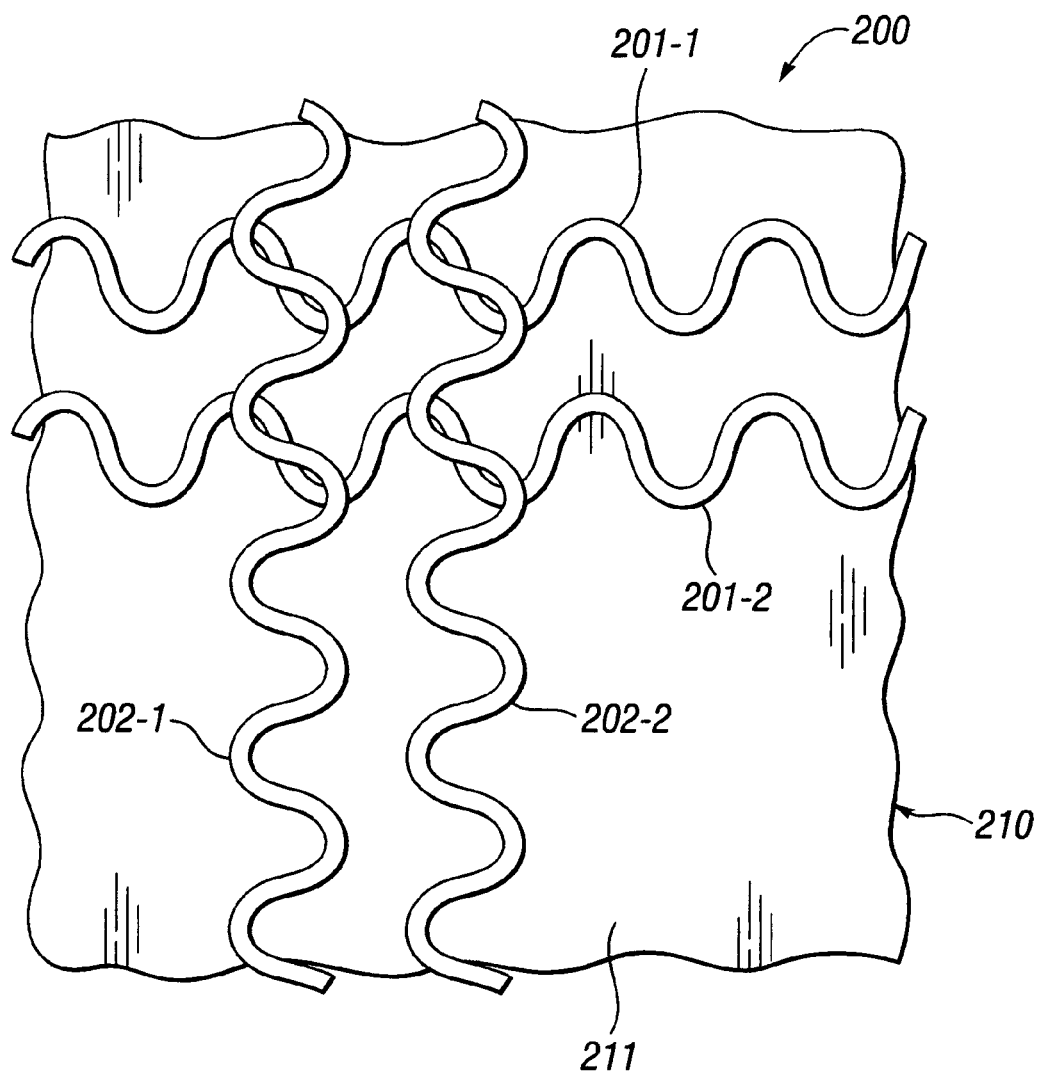
FIG. 21A is a fragmentary upper perspective view of a single layer fabric substrate sensor array in which both upper row and lower column piezoresistive threads are sinuously arranged and fastened to the same side of a single insulating substrate sheet.

FIG. 21A illustrates another modification 200, which row and column piezoresistive threads 201, 202 are both sinuously arranged and attached to the upper surface 211 of an insulating substrate sheet 210, in the manner shown in FIG. 16.

Figure 22A:
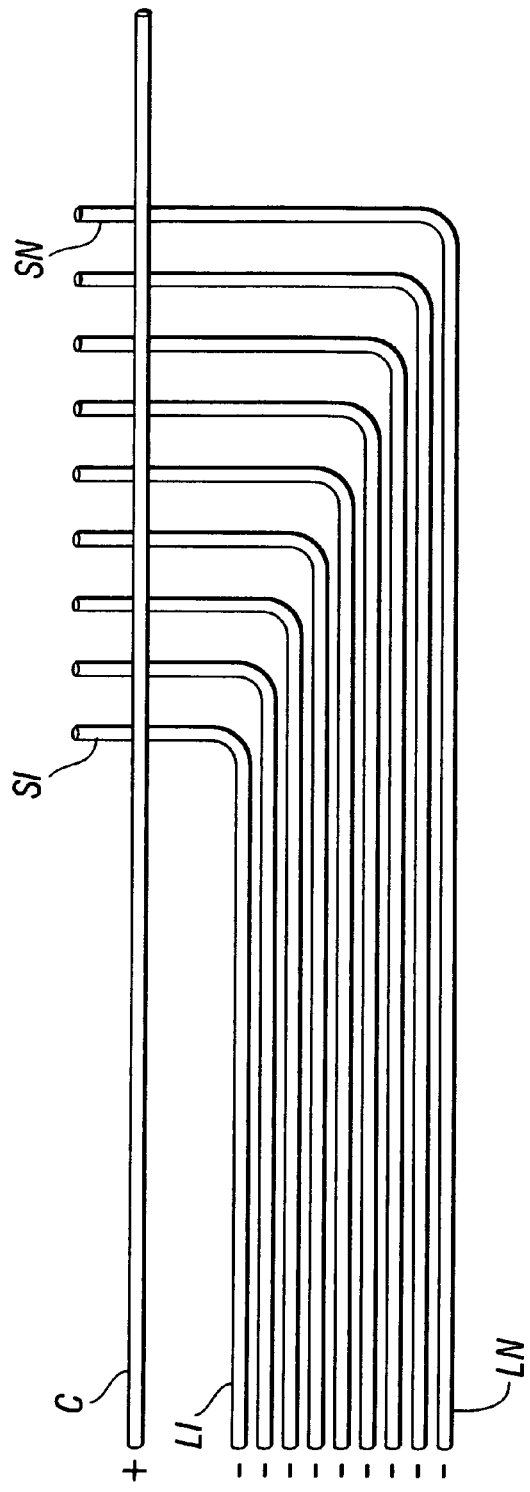
FIG. 22A is a schematic diagram showing the number of conductive lead-outs required to measure the resistance of individual sensor elements in a linear array.

FIG. 22A illustrates the number of conductive leads required to measure the resistance of individual elements of a linear array of sensor elements, to thus determine numerical values of force or pressure exerted on each sensor element. As shown in FIG. 22A a single common lead-out conductor C is connected to a linear array of intersecting lead-out conductors Li through Ln to form a plurality of sensor elements SI through Sn, by piezoresistive material at each intersection point. Thus, for a total of n sensors S, there are required a total R equal to n+1 lead-out conductors to measure the individual resistance of each sensor element SI through Sn and hence determine the forces F1 through Fn exerted on each individual sensor element.

Figure 22B:
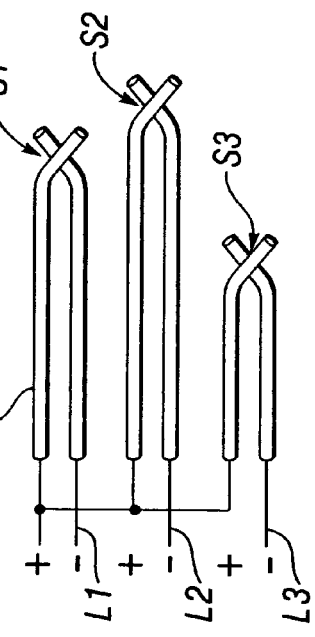
FIG. 22B shows sensor elements which do not have to be in a linear arrangement.

FIG. 22B shows a plurality of sensor elements Sn+1, Sn+2, Sn+3 which are not necessarily arranged in a linear array, being located, for example, on individual finger tips. As shown in FIG. 22B, n+1 lead-out conductors are also required for this configuration.

FIG. 7 illustrates the electrical resistance of a one-inch square piezoresistive force sensor element 48 using a piezoresistive sheet 37 having the formulation listed for an example sensor array 30 shown in FIGS. 1 and 2, and fabricated as described above, as a function of normal force or pressure exerted on the upper surface 47 of upper substrate sheet 33 of sensor array 30. As shown in FIG. 7, the resistance varies inversely as a function of normal force.

As shown in FIG. 1, row conductive threads 31-1 through 31-m, in vertical alignment with column conductive threads 32-1 through 32-n form with piezoresistive layer sheet 37 between the column and row conductive threads a m×n rectangular matrix array of m×n force elements 48.

If upper and lower electrical connections to each sensor element 48 were electrically isolated from connections to each other sensor element, a separate pair of lead-out conductors for each of the sensors, would be required, i.e., a total of 2Q lead-out conductors for Q sensor elements or, if a single common electrode lead-out were employed as shown in FIG. 22, a total of Q+1 lead-outs would be required.

Figure 23:
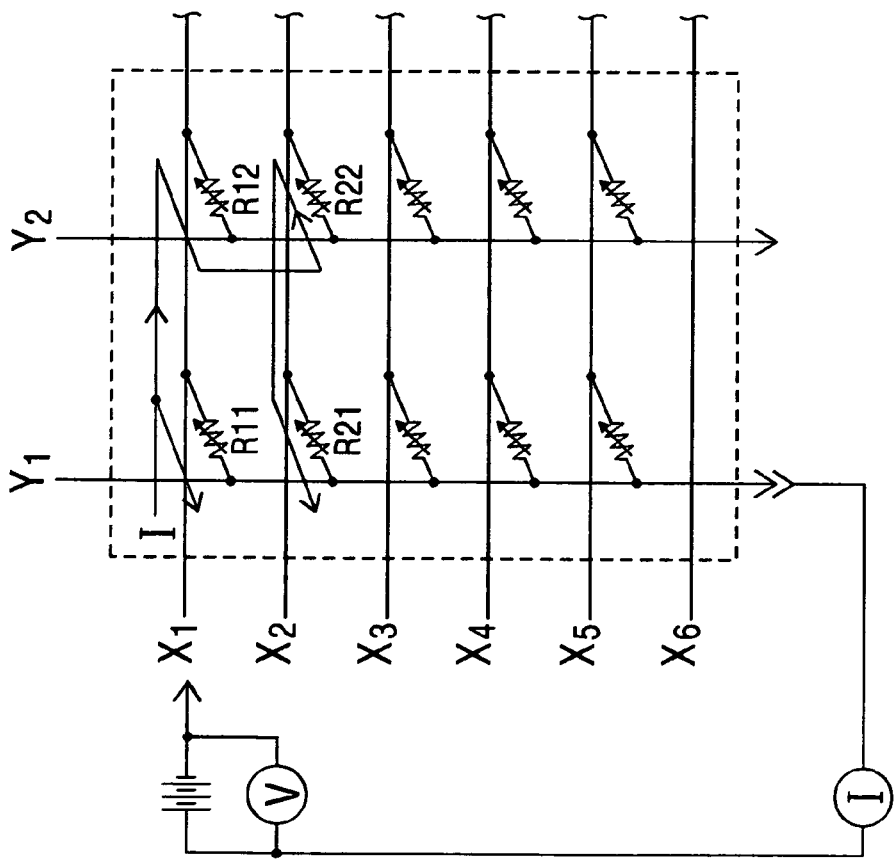
FIG. 23 is a schematic diagram showing a reduced number of lead-outs required for matrix addressing an array of sensor elements arranged in a matrix array.

Preferably, as shown in FIG. 1, sensor array 30 is arranged into a matrix of m rows and n columns, thus requiring only R=m×n lead-out conductors. However, as shown in FIG. 23, if matrix addressing of sensor array 30 is used to measure the resistance of individual sensors 48 to thereby determine normal forces exerted on the sensors, there is a substantial cross-talk between the resistance on an addressed sensor 48 and non-selected sensors because of parallel current paths to non-addressed sensors. To overcome this cross-talk problem, the present inventor has developed a method for modifying sensors 48 to give them a diode-like characteristic. As may be confirmed by referring to FIG. 24, the cross-talk between sensor elements 40 which have a non-bilateral, polarity-sensitive transfer function, mitigates the cross-talk problem present in the matrix of symmetrically conductive sensors 48 shown in FIG. 23.

Sensor elements 48 are modified to have a diode-like characteristic by modifying the preparation of piezoresistive layer sheet 37, as follows: First, a piezoresistive layer sheet 37 is prepared by the process described above. Then, either the upper surface 40 or the lower surface 41 of the piezoresistive coating 37A of piezoresistive sheet 37 is modified to form thereon a P-N, semiconductor-type junction.

Modification of piezoresistive coating 37A to form a P-N junction is performed by first preparing a slurry which has the composition of one of the three example mixtures described above, but modified by the addition of 5 ml each of copper oxide (CuO) in the form of a fine powder of 50-micron size particles, and 5 ml of cuprous oxide ($Cu_2O$) in the form of a fine powder of 50-micron size particles and thoroughly stir-mixing the foregoing ingredients. The resultant solution is then reduced using about 30 mg of solution of sodium borohydride, also known as sodium tetrahydroborate ($NaBH_4$) or ammonium phosphate, to form a solution having a pH of about 5.5. The solution is then coated onto the upper surface 40 or lower surface 41 of piezoresistive coating 37B on piezoresistive sheet 37. This coating process is performed using a roller coating process which results in about 0.5 ml of solution per square centimeters being applied. The surface coating is then allowed to air-dry at room temperature and a relative humidity of less than 20%, for 4 hours. After the coated surface has dried, it functions as a P-type semiconductor, while the uncoated side of coating 37B functions as an N-type semiconductor of P-N junction diode.

Figure 29:
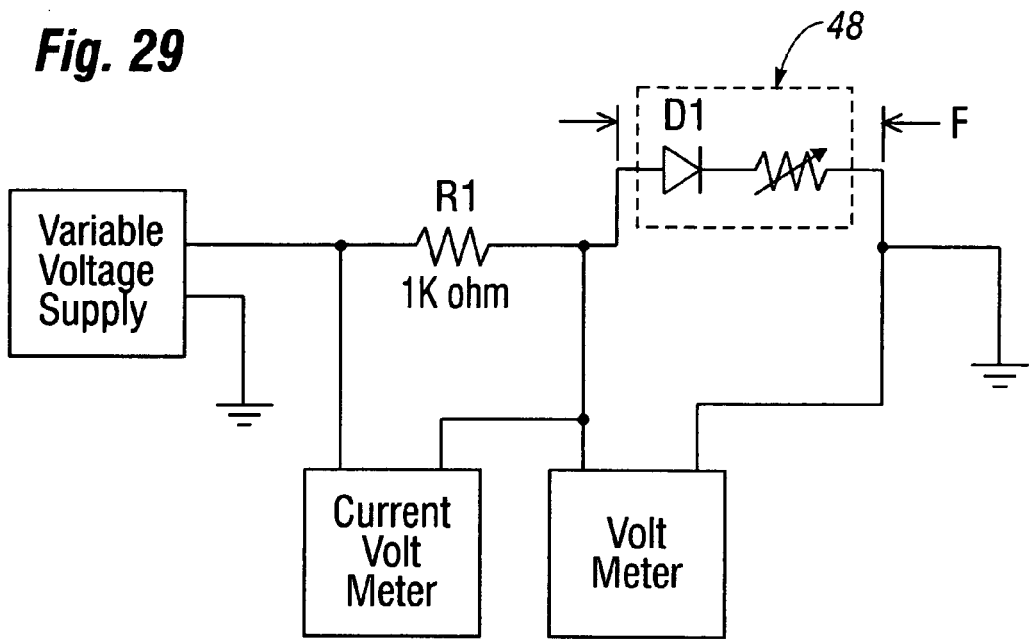
FIG. 29 is a partly schematic view of a preferred modification of sensor elements of the array of FIG. 1, in which sensor elements of the array have been modified to provide them with P-N, diode-type junctions.
Figure 30:
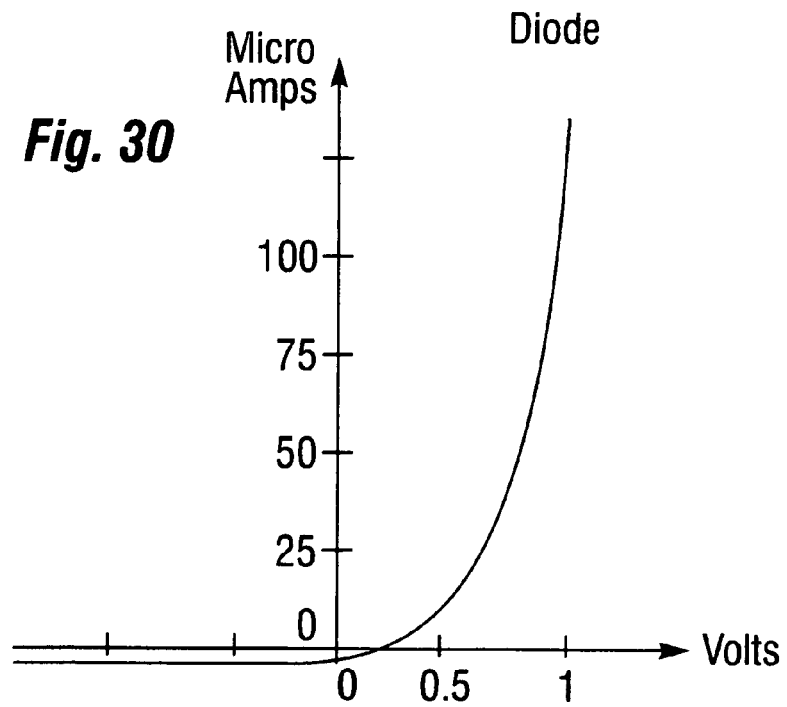
FIG. 30 is a current-versus-voltage diagram for the sensor elements of FIG. 27.
Figure 31:
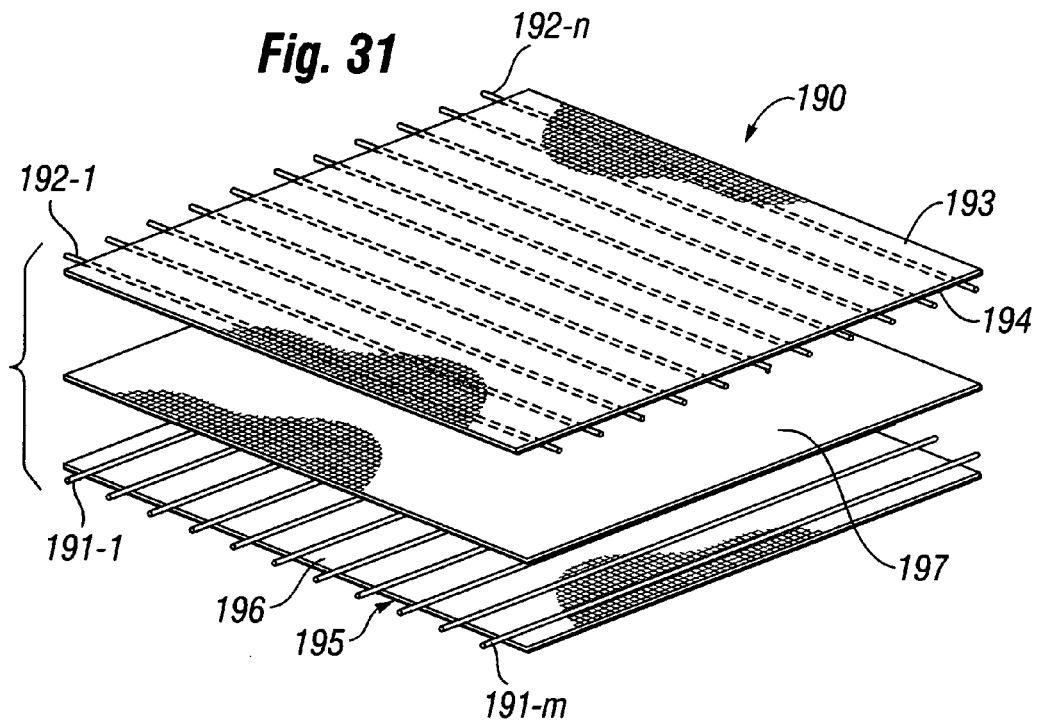
FIG. 31 is an exploded perspective view of another embodiment of a force sensor array according to the present invention.
Figure 32:
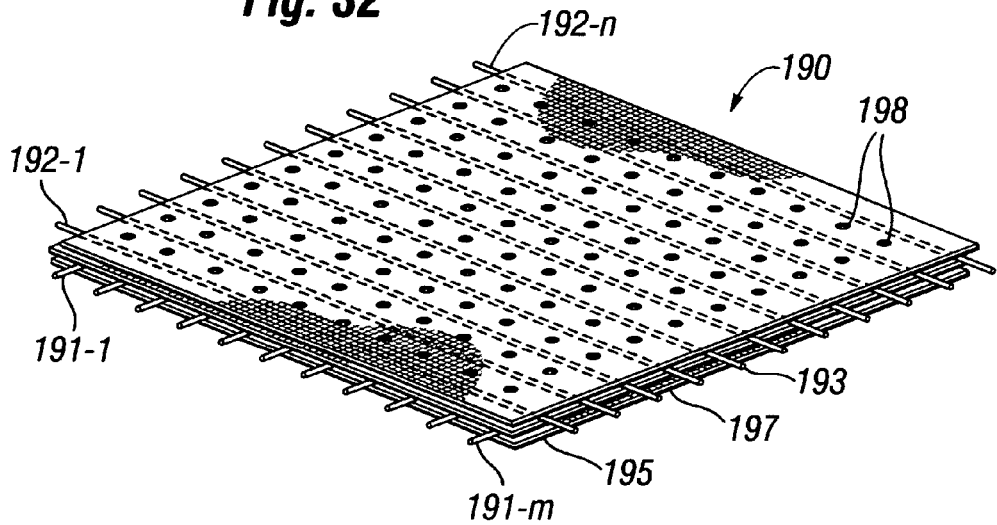
FIG. 32 is a perspective view of the sensor array of FIG. 31.

FIG. 29 illustrates a sensor element 48 which has been prepared as described above to give the sensor a diode-like characteristic, and a circuit for obtaining the I-V (current versus voltage) transfer function of the sensor. FIG. 30 shows a typical I-V curve for sensor elements 48 of FIG. 29.

As stated above, the advantage of modifying sensor elements 48 of sensor array 30 by adding a semi-conductive layer that acts like a diode is that it reduces cross talk between sensors. As is shown in FIG. 23, this cross-talk occurs because of the so-called "completing the square" phenomenon, in which three connections are made in a square matrix array of three non-addressed resistors that form the three corners of a square. Thus, any two connections in a vertical column and a third one in the same row function as either connection in an X-Y array of conductors. The resistor at the fourth corner of the square shows up as a phantom in parallel with an addressed resistor because the current can travel backwards through that resistor, and forward through the other resistors. Care and additional expense must be taken in the electronics to eliminate the contribution of this phantom. For example, if, as is shown in FIG. 23, a potential V is applied between row and column conductors $X_1Y_1$, to thereby determine the resistance of piezoresistive sensor resistance $R_{11}$, reverse current flow through "phantom" resistor $R_{22}$ would cause the sum of resistances $R_{12}+R_{22}+R_{22}$ to shunt $R_{11}$, resulting in the parallel current flow paths indicated by arrows in FIG. 23, which in turn would result in the following incorrect value of resistance:

$$R_{x1}y_1 = R_{11}//(R_{12}+[R_{22}]+R_{21}), R_{x1}y_1 = R_{11}(R_{13}+[R_{22}]+R_{21})/(R_{11}+R_{12}+[R_{22}]+R_{21}),$$

where brackets around a resistance value indicate current flow in a counterclockwise direction through that resistor, rather than clockwise, i.e., diagonally downwards towards the left. Thus, for example, if each of the four resistances listed above had a value of 10 ohms, the measured value of $R_{11}$ would be:

$R_{11}=10(10+10+10)/(10+10+10+10)=300/40=7.5$ ohms, i.e., 25% below the actual value, 10 ohms, of $R_{11}$. If the resistance values of $R_{12}$, $R_{22}$ and $R_{21}$ of the three non-addressed piezoresistive sensor element 48 were each lower, e.g., 1 ohm, because of greater forces concentrated on those sensor elements 48, the measured value of $R_{11}$ would be:

$R_{11}=10(1+1+1)/(10+1+1+1)=30/13=2.31$ ohms, i.e., a value of about 77 percent below the actual value of $R_{11}$.

Figure 24:
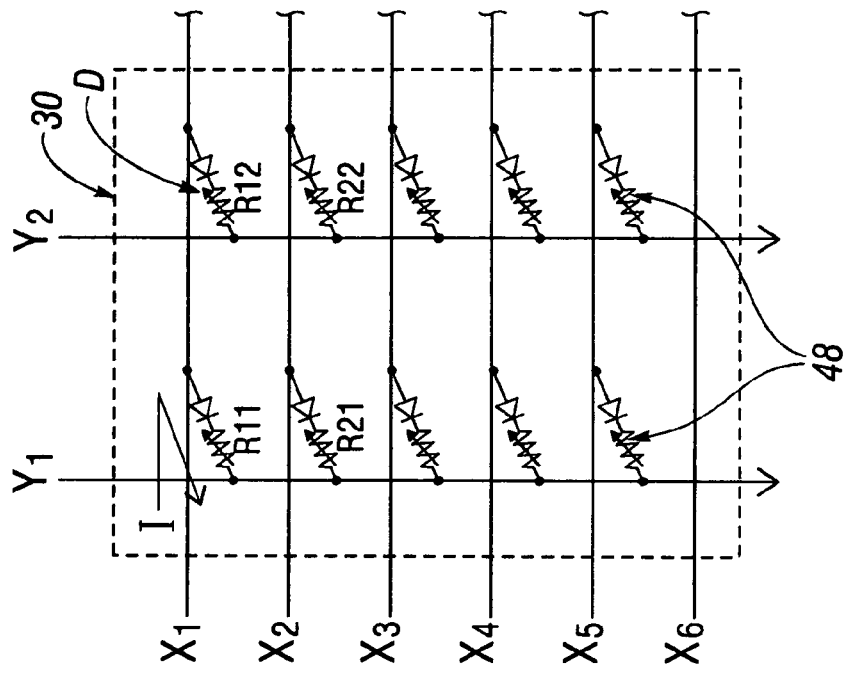
FIG. 24 is a schematic diagram showing sensor elements of the array of FIG. 23 modified to include a diode junction.

On the other hand, by placing a diode in series with each piezoresistive sensor element 48, as shown in FIG. 24, the electrical resistance of an element measured in a reverse, counterclockwise direction a test current flow through the sensor element, e.g., $R_{22}$, would be for practical purposes arbitrarily large, or infinity compared to the clockwise forward paths of current through the other resistances shown in FIGS. 23 and 24. In this case, the measured resistance value for a 2×2 matrix of four resistances each having a value of 10 ohms would be:

$R_{x1y1}=10(1+\infty+1)/(10+1+\infty+1)=10$ ohms, the correct value.

Thus, modifying each sensor element 48 to include a p-n junction thereby give the sensor element a diode-like characteristic electrically isolates, i.e., prevents backward current flow, through each sensor element 48. This enables the correct value of electrical resistance of each sensor element 48 and hence forces exerted thereon to be measured accurately $R_{x1}y_1$ using row and column matrix addressing rather than requiring a separate pair of conductors for each sensor element.

FIG. 25 illustrates a force measuring apparatus 150 according to the present invention. The apparatus may use any of the types of sensor arrays described above, but in a particular example shown in FIG. 25 uses a sensor array 70 of the type shown in FIG. 5.

As shown in FIG. 25, force measuring apparatus 150 used four sensor arrays 70-1, 70-2, 70-3 and 70-4, each having a matrix of 16 row conductive threads by 16 column conductive threads. The four arrays are arranged in a square matrix, to thus form a composite sensor array 70-C consisting of 32 rows×32 columns of conductive threads having formed at their intersection 32×32=1,024 sensor elements 88. As shown in FIG. 25, each of the 32 row conductive thread lead-out wires and each of the 32 column conductive thread lead-outs is connected to a separate electrically conductive connector pin of a plurality of connector pins 154-1 through 154-64 of a pair of electrical interface connectors 153-1, 153-2.

Figure 26:
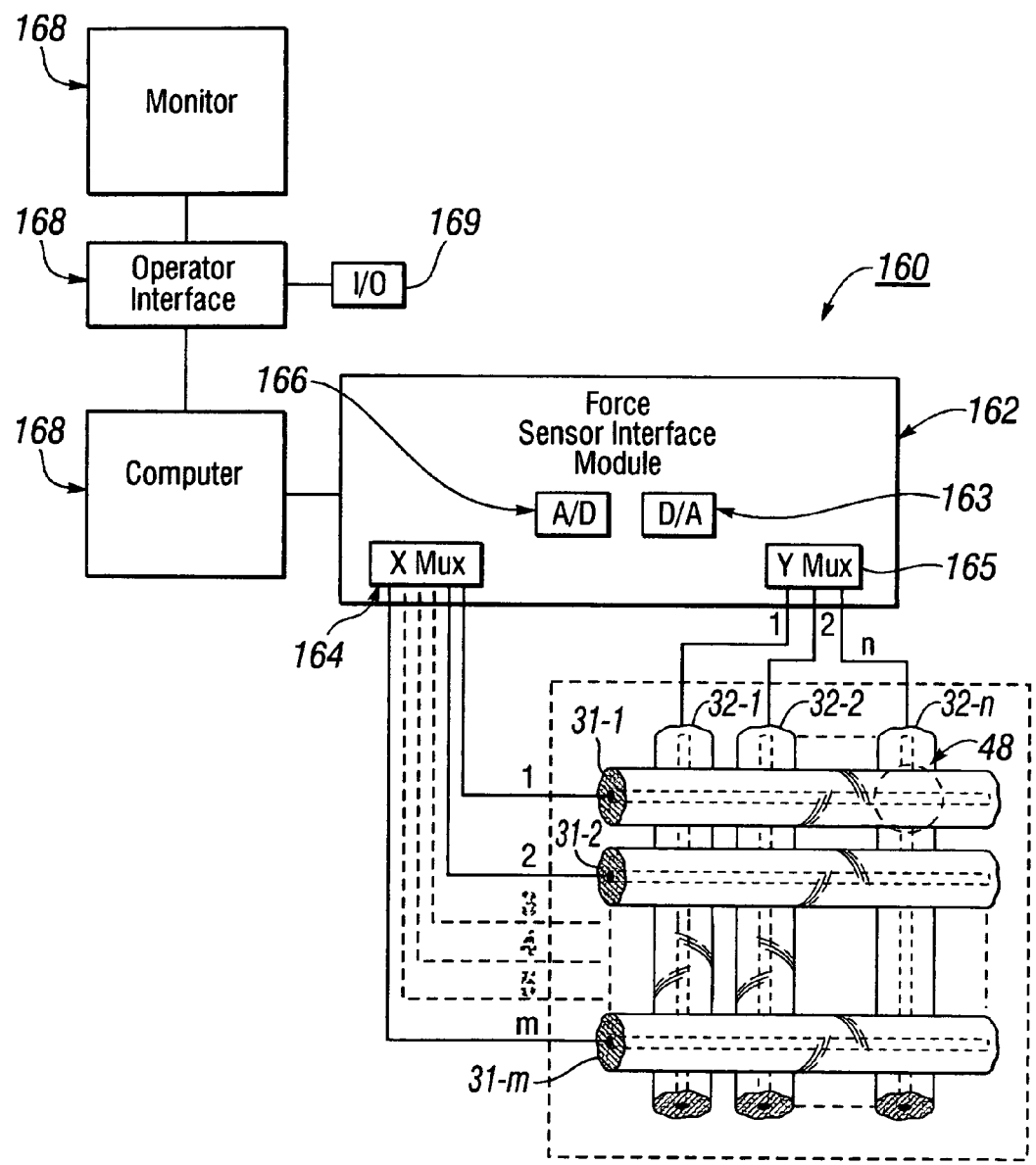
FIG. 26 is a block diagram showing the sensor array of FIGS. 1 and 3 interconnected with signal processing and display circuitry to comprise a force measurement system.

FIG. 26 illustrates a force measurement system 160 which utilizes the force 6 sensor apparatus 150 described above.

As shown in FIG. 26, force measurement system 160 includes a computer 161 which is bidirectionally coupled to force sensor array 70 of force sensor apparatus 160 through a force sensor interface module 162. The sensor interface module 162 includes a Digital-to-Analog Converter (DAC) 163 for generating in response to control signals from computer 161 test voltages or currents which are directed to matrix-addressed individual force sensors 88.

As shown in FIG. 26, individual force sensor elements 88 are addressed by connecting one terminal of a current or voltage source controlled by DAC 163 to a selected one of X-row conductors 51-*l*-51-*m* by an X multiplexer 164, and connecting the other terminal of the source to a selected one of Y-column conductors 52-*l*-52-*m* by a Y multiplexer 165. Sensor interface module 162 also included an Analog-to-Digital Converter (ADC) 166 which measures the voltage drop or current through a sensor element 88 resulting from application of a test current or voltage, and inputs the measured value to computer 161. Using predetermined scale factors, computer 161 calculates the instantaneous value of electrical resistance of a selected addressed sensor element 88, and from that resistance value, a corresponding normal force instantaneously exerted on the addressed sensor.

In response to control signals cyclically issued by computer 161, X multiplexer 164 and Y multiplexer 165 are used to cyclically measure the resistance of each force sensor element 88, at a relatively rapid rate of, for example, 3,000 samples per second, enabling computer 161 to calculate the force exerted on each force sensor element 88 at that sampling rate. Measurement system 160 includes an operator interface block 167 which enables values of force or pressures measured by sensor elements 88 to be displayed as numerical values and/or a graph or pressure/force map on the display screen of a computer monitor 168, or outputted to a peripheral device such as a printer, or a network such as the internet, through an I/O block 169.

Figure 27B:
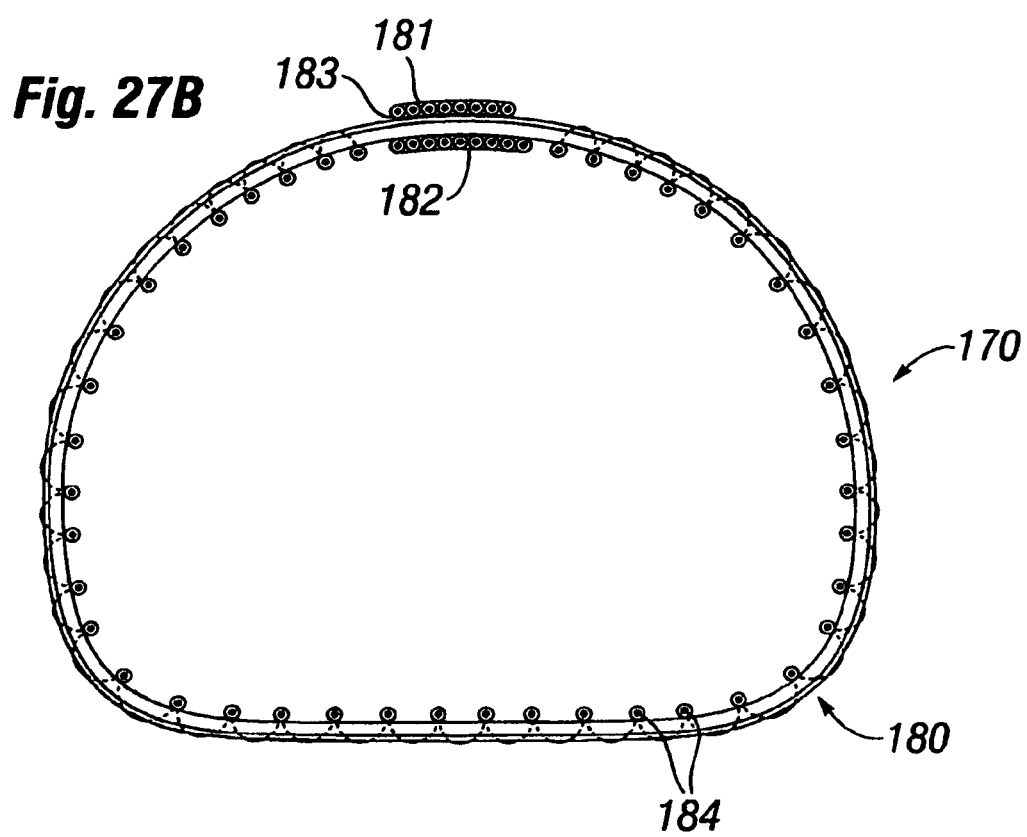
FIG. 27B is a horizontal transverse sectional view of the sock of FIG. 27A.
Figure 28:
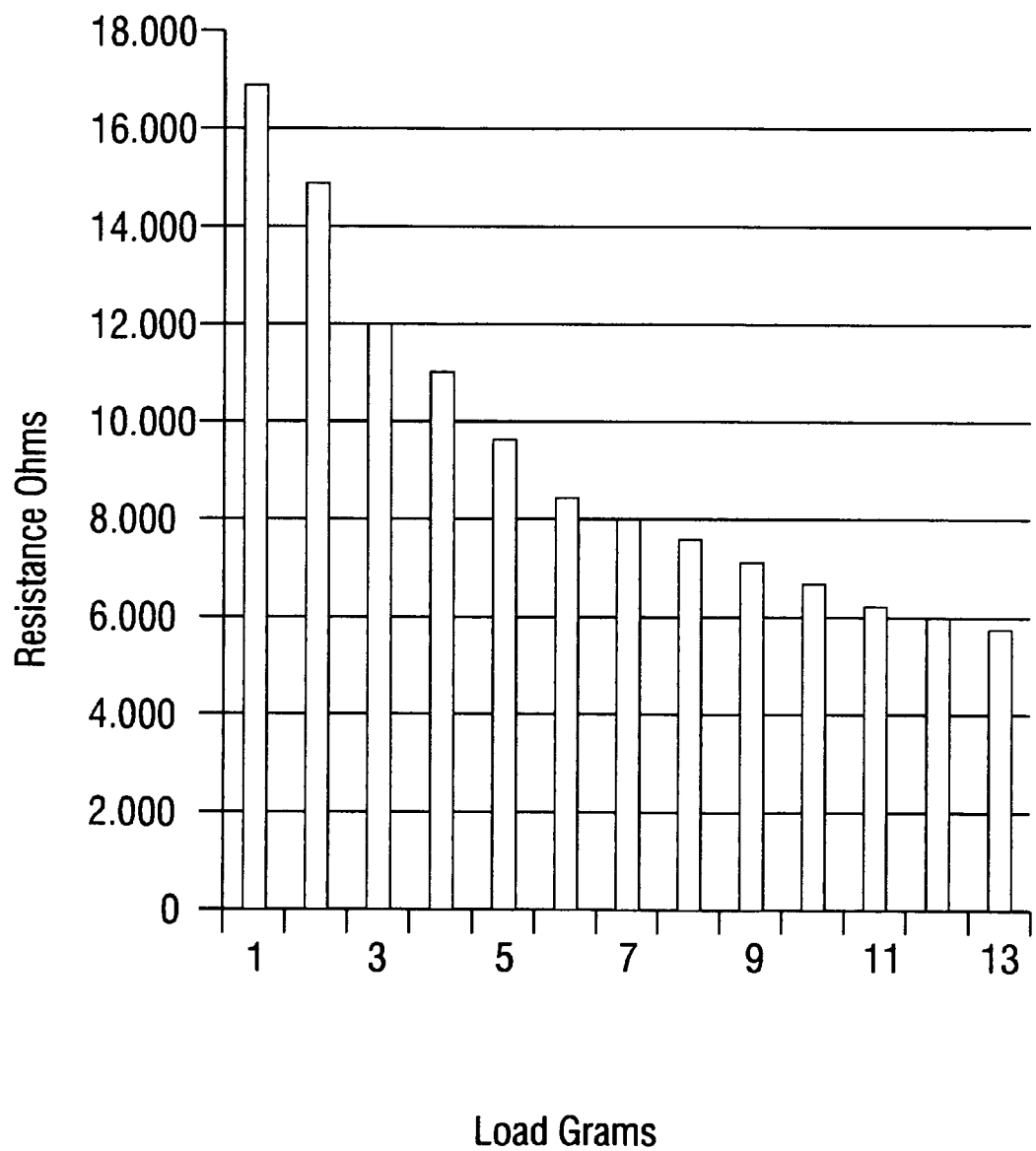
FIG. 28 is a typical electrical resistance-versus-normal force diagram for sensors according to the present invention.

FIGS. 27A and 27B illustrate a sock 170 which includes one of the novel sensor arrays employing conductive threads which were described above, such as the single layer, fabric substrate piezoresistive thread sensor array shown in FIG. 14-16 or 17-20.

As shown in FIG. 17, sock 170 which includes a single layer fabric force sensor array 180 that is a modification of the planar force sensor array 120 shown in FIGS. 14-16 and described above. The modification of force sensor array 120 to form force sensor array 180 may be best visualized by considering that the left and right side edges of the array 120 are brought upwards from the plane of the page to meet and form a hollow cylindrical tube.

Row conductor threads protruding 121 from the aligned edges of the array are then electrically conductively fastened to a first, row conductor ribbon cable 181. Column conductive threads protruding from one edge of the rolled-up array are electrically conductively fastened to a second, column conductor ribbon cable 182. Outer ends 183, 184 who protrude from an edge of array 120 are electrically connected to a resistance measuring circuit as shown in FIG. 26 and described above.

FIGS. 31-34 illustrate modifications of fabric substrate force sensor arrays using conductive threads according to the present invention, in which the conductive threads are fixed to a fabric substrate sheet without the use of sewn stitching by adhesive applied directly to a conductive thread. Thus, a first, three-layer fabric sensor array 190 includes a plurality of parallel, spaced apart row conductive elastic threads 191 which are adhesively bonded to the lower surface 194 of an upper stretchable fabric substrate sheet 193 made of 3 mil thick polyester or either of the two Milliken fabrics described above. Sensor array 190 also includes a plurality of parallel spaced apart column conductive elastic threads 192 which are adhesively bonded to an upper surface 196 of a lower stretchable fabric substrate sheet 195. A thin sheet of stretchable fabric prepared to give it a piezoresistive property in the manner described above comprises a central piezoresistive layer 197 which is positioned between row and column conductive threads 191, 192. The foregoing three layers are then stacked on top of one another and dots of glue injected through the mesh openings of the fabric substrate of all three layers to adhere them together and thus form a completed sensor array 190.

Figure 33:
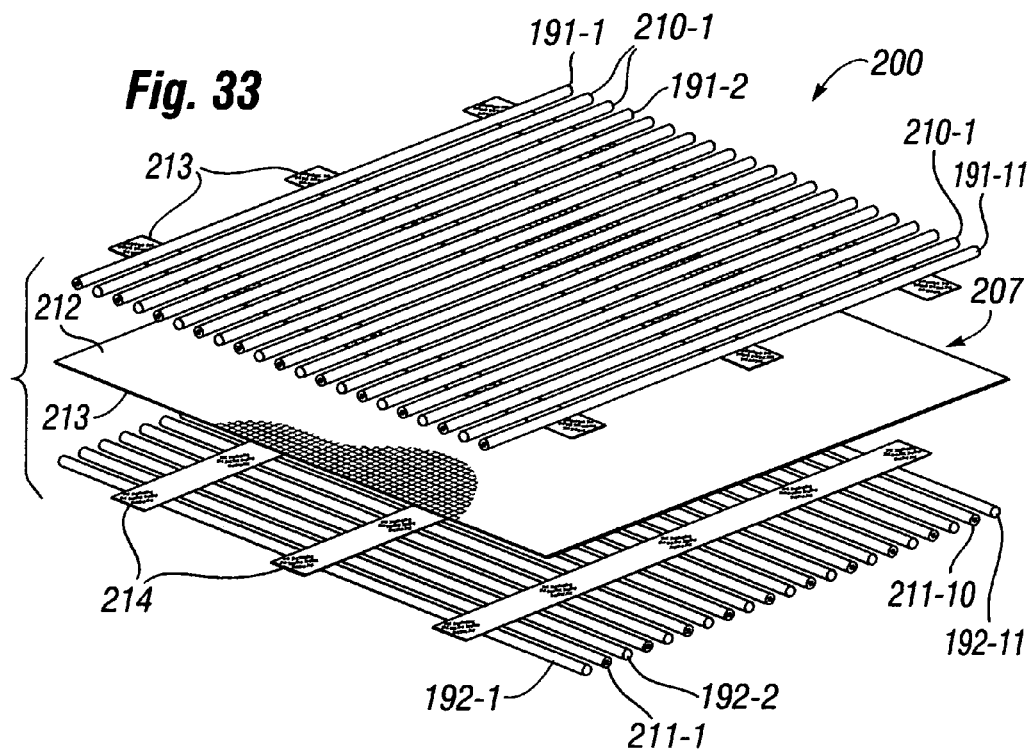
FIG. 33 is an exploded perspective view of components of another embodiment of a force sensor array according to the present invention.
Figure 34:
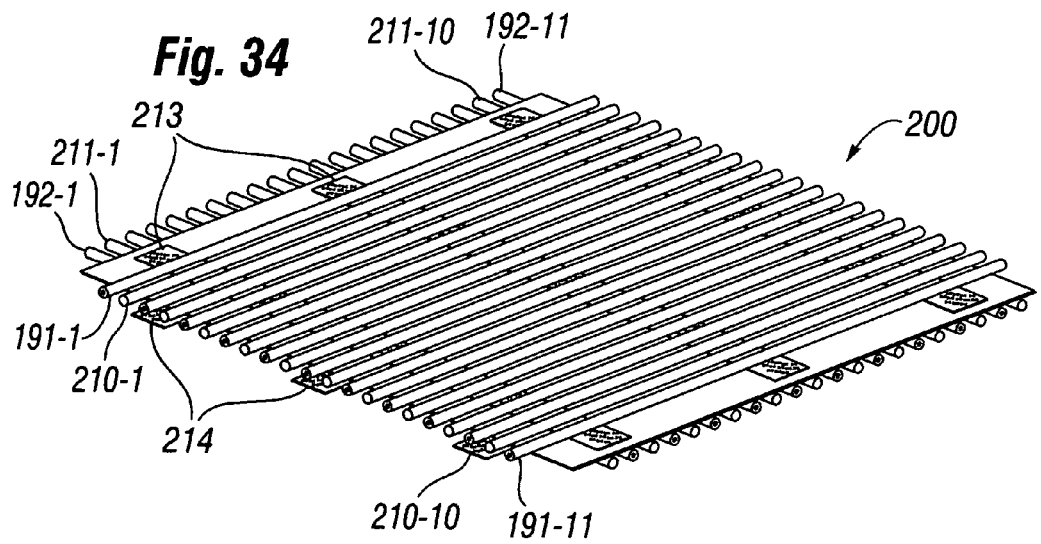
FIG. 34 is a perspective view of the sensor array of FIG. 33.

Sensor array 200, shown in FIG. 33, utilizes a single substrate sheet 207. Conductive row and column threads 191, 192, separated by insulating threads 210, 211, are adhered to upper surface 212 and lower surface 213 of sheet 207 by double-stick tape strips 213, 214.

What is claimed is:

1. A force sensing transducer for measuring force exerted thereon, said transducer comprising:
   a. an elongated, elastically stretchable, electrically conductive row thread,
   b. an elongated, elastically stretchable electrically conductive column thread,
   c. the elastic stretchability of at least one of said row and column conductive threads being at least as great as one percent, and
   d. a piezoresistive material located between and in electrically conductive contact with said row and column threads.

2. The force sensing transducer of claim 1 wherein said piezoresistive material is further defined as being contained in an elastically deformable coating on at least one of said row and column conductive threads.

3. The force sensing transducer of claim 2 wherein said row and column threads are attached to inner facing sides of a pair of elastically deformable substrate sheets.

4. The force sensing transducer of claim 3 wherein at least one of said substrate sheets is made of a woven fabric.

5. The force sensing transducer of claim 4 wherein at least one of said row and column conductive threads is attached to a substrate sheet by a sewn insulating thread.

6. The force sensing transducer of claim 2 wherein said row and column conductive threads are attached to one side of an insulating elastically deformable substrate sheet.

7. The force sensing transducer of claim 6 wherein at least one of said substrate sheets is made of a woven fabric.

8. The force sensing transducer of claim 7 wherein at least one of said row and column conductive threads is attached to a substrate sheet by a sewn insulating thread.

9. The force sensing transducer of claim 1 wherein said piezoresistive material is further defined as being contained in an elastically deformable piezoresistive substrate sheet containing a piezoresistive substance contacted by said conductive row thread, and contacted by said conductive column thread.

10. The force sensing transducer of claim 9 wherein said piezoresistive substrate sheet is impregnated with said piezoresistive substance.

11. The force sensing transducer of claim 9 wherein said row and column threads are attached to opposite planar surfaces of said piezoresistive substrate sheet.

12. The force sensing transducer of claim 11 wherein at least one of said row and column threads is attached to an elastically deformable substrate sheet.

13. The force sensing transducer of claim 1 wherein at least either of said row and column conductive threads has a polymer core.

14. The force sensing transducer of claim 13 wherein said polymer core is in the form of a thread.

15. The force sensing transducer of claim 13 wherein said polymer core is in the form of a yarn.

16. The force sensing transducer of claim 13 wherein said polymer core has formed thereon an electrically conductive coating.

17. The force sensing transducer of claim 1 wherein the elastic stretchability of at least either of said row and column conductive threads is at least as great as about ten percent.

18. The force sensing transducer of claim 1 wherein the elastic stretchability of at least either of said row and column conductive threads is at least as great as about thirty percent.

19. The force sensing transducer of claim 1 wherein said conductive row thread comprises one of a plurality m of parallel conductive row threads.

20. The force sensing transducer of claim 19 wherein said conductive column thread is angled with respect to said conductive row threads.

21. The force sensing transducer of claim 20 wherein said conductive column thread comprises one of a plurality n of conductive column threads.

22. The force sensing transducer of claim 21 wherein said conductive row threads are located in a first surface.

23. The force sensing transducer of claim 22 wherein said conductive column threads are located in a second surface.

24. The force sensing transducer of claim 23 wherein said first and second surfaces are mutually parallel.

25. The force sensing transducer of claim 1 wherein at least either of said row and column conductive threads is disposed in a path which is sinuously arranged with respect to a line joining first and second ends of said thread.

26. The force sensing transducer of claim 1 wherein at least either of said row and column conductive threads is made from a polymer selected from the group consisting of monofilament thread, woven thread and woven yarn.

27. A force sensing transducer for measuring force exerted thereon, said transducer comprising:
   an elongated, elastically stretchable, electrically conductive row thread;
   an elongated, elastically stretchable electrically conductive column thread, at least one of said row and column conductive threads having an elastic stretchability at least as great as about one percent, at least one of said row and column conductive threads also having a polymer core on which is formed an electrically conductive coating; and
   a piezoresistive material located between and in electrically conductive contact with said row and column threads, said piezoresistive material being defined as a piezoresistive coating formed on said electrically conductive coating.

28. A force sensing transducer for measuring force exerted thereon, said transducer comprising:
   an elongated, elastically stretchable, electrically conductive row thread;
   an elongated, elastically stretchable electrically conductive column thread, at least one of said row and column conductive threads having an elastic stretchability at least as great as about one percent, at least one of said row and column conductive threads also having a polymer core; and a piezoresistive material located between and in electrically conductive contact with said row and column threads, said piezoresistive material being defined as a piezoresistive coating formed on said polymer core.

29. A force sensing transducer array for measuring forces exerted on spatially separated parts thereof, said transducer array comprising:
   a. a plurality of m elongated elastically stretchable electrically conductive row threads which are spatially separated from one another,
   b. plurality n of elongated elastically stretchable electrically conductive column threads which are spatially separated from one another,
   c. the elastic stretchability of at least one of said row and column conductive threads being at least as great as one percent, and
   d. a piezoresistive material located between and in electrically conductive contact with said row and column conductive threads to thus form at p=m×n intersections thereof a plurality of p sensor elements.

30. The force sensing transducer array of claim 29 wherein said piezoresistive material is further defined as including a circuit element having a non-bilateral electrical impedance characteristic in series with at least one of said p sensors for reducing cross talk between measurements of electrical impedance of said sensor elements by matrix addressing of selected pairs of row and column conductive threads.

31. The force sensing transducer array of claim 30 wherein said non-bilateral electrical impedance characteristics if further defined as being a diode-like characteristic.

32. The force sensing transducer array of claim 31 wherein said piezoresistive material is further defined as including electrically conductive particles suspended in an elastomeric solid solution.

33. The force sensing transducer array of claim 32 wherein said diode-like characteristic is formed by coating a surface of said piezoresistive material with at least one metallic oxide.

34. The force sensing transducer array of claim 33 wherein said metallic oxide is further defined as including at least one copper oxide.

35. The force sensing transducer array of claim 32 wherein said piezoresistive material is further defined as being contained in an elastically deformable coating on at least one of said row and column conductive threads.

36. The force sensing transducer of claim 32 wherein said piezoresistive material is further defined as being contained in an elastically deformable piezoresistive substrate sheet containing a piezoresistive substrate contacted by said conductive row thread, and contacted by said conductive column thread.

37. A force sensing transducer array for measuring forces exerted on spatially separated parts thereof, said transducer array comprising:

a plurality of elongated elastically stretchable electrically conductive row threads which are spatially separated from one another, said electrically conductive row threads each including a polymer core onto which is formed an electrically conductive coating;

a plurality of elongated elastically stretchable electrically conductive column threads which are spatially separated from one another, said electrically conductive column threads each including a polymer core onto which is formed an electrically conductive coating; and a piezoresistive material contained in an elastically deformable coating on at least one of the electrically conductive coatings of at least one of the plurality of row and column conductive threads, wherein said plurality of row and column conductive threads define a plurality of sensors at a plurality of intersections of the row and column conductive threads.

38. The force sensing transducer array of claim 37 wherein said electrically conductive row threads and said electrically conductive column threads are attached to an elastically deformable substrate sheet.

* * * * *